United States Patent
Nakamura et al.

(10) Patent No.: US 8,847,000 B2
(45) Date of Patent: Sep. 30, 2014

(54) COMPOSITION FOR ALKYLATION AND METHOD FOR DETOXIFYING A HARMFUL COMPOUND BY USING THE COMPOSITION

(75) Inventors: Koichiro Nakamura, Tokyo (JP); Akihiro Hishinuma, Tokyo (JP); Shinji Kamiya, Tokyo (JP)

(73) Assignee: Nippon Sheet Glass Company, Limited, Tokyo (JP)

(*) Notice: Subject to any disclaimer, the term of this patent is extended or adjusted under 35 U.S.C. 154(b) by 717 days.

(21) Appl. No.: 12/309,494

(22) PCT Filed: Jul. 26, 2007

(86) PCT No.: PCT/JP2007/000797
§ 371 (c)(1),
(2), (4) Date: Apr. 15, 2009

(87) PCT Pub. No.: WO2008/012950
PCT Pub. Date: Jan. 31, 2008

(65) Prior Publication Data
US 2009/0326313 A1 Dec. 31, 2009

(30) Foreign Application Priority Data

Jul. 26, 2006 (JP) .................................. 2006-203686
Jan. 5, 2007 (WO) .................. PCT/JP2007/050368

(51) Int. Cl.
| | |
|---|---|
| A62D 3/37 | (2007.01) |
| C09K 3/00 | (2006.01) |
| C07F 15/06 | (2006.01) |
| A62D 3/33 | (2007.01) |
| B01J 31/18 | (2006.01) |
| C07C 391/00 | (2006.01) |
| A62D 101/43 | (2007.01) |
| A62D 101/24 | (2007.01) |

(52) U.S. Cl.
CPC .............. *C07F 15/06* (2013.01); *A62D 2101/43* (2013.01); *A62D 2101/24* (2013.01); *A62D 3/33* (2013.01); *A62D 3/37* (2013.01); *B01J 31/1815* (2013.01); *B01J 2531/845* (2013.01); *C07C 391/00* (2013.01); *B01D 2257/60* (2013.01); *B01J 2531/025* (2013.01); *A62D 2203/04* (2013.01)
USPC ....................... 588/319; 252/188.1; 252/188.2

(58) Field of Classification Search
None
See application file for complete search history.

(56) References Cited

U.S. PATENT DOCUMENTS

| | | | | | |
|---|---|---|---|---|---|
| 3,007,916 | A | * | 11/1961 | Bernhauer et al. | .......... 536/26.41 |
| 6,117,333 | A | * | 9/2000 | Frankiewicz et al. | .......... 210/705 |
| 2008/0145918 | A1 | * | 6/2008 | Hishinuma et al. | ........ 435/262.5 |

FOREIGN PATENT DOCUMENTS

| | | |
|---|---|---|
| WO | 2005/100268 | 10/2005 |
| WO | 2006/070885 | 7/2006 |

OTHER PUBLICATIONS

Shimakoshi et al. Bull. Chem. Soc. Jpn, 78, 859-863, 2005.*
Jameson et al. J. Chem. Ed. 75, 447-450, 1998.*
Applied Organometallic Chemistry, 12, 635-641, 1998.*
Braman et al. Enviromental Health Perspectives, 19, 1-4, 1977.*
Holliger et al., FEMS Microbiology Reviews 22 (1999) 383-398.*
Cullen, et al., "Preparation of Arsinocobaloximes and the Crystal Structure of [(CH$_3$)(C$_6$H$_5$)As(O)Co$^{III}$(dmgH)(dmg)]$_2$Co$^{II}$", Journal of the American Chemical Society, vol. 101, No. 23, 6898-6904 (1979).
Thompson-Eagle, et al., "Selenium Biomethylation in an Alkaline, Saline Environment", Water Research, vol. 25, No. 2, 231-240 (1991).
Wehmeier, et al., "Investigations into the role of methylcobalamin and glutathione for the methylation of antimony using isotopically enriched antimony (V)", Applied Organometallic Chmistry, vol. 18, 631-639 (2004).
Kaise, et al., "Cytotoxicological Aspects of Organic Arsenic Compounds Contained in Marine Products Using the Mammalian Cell Culture Technique", Applied Organometallic Chemistry, vol. 12, 137-143 (1998).
Zakharyan et al., "Arsenite methylation by methylvitamin B$_{12}$ and glutathione does not require an enzyme," Toxicology and Applied Pharmacology, 1999, vol. 154, pp. 287-291.
Pergantis et al., Investigating the non-enzymatic methylation of arsenite by methylcobalamin B$_{12}$ using high-performance liquid chromatography on-line with inductively coupled plasma-mass spectrometry, J. Anal. At. Spectrom., 2004, vol. 19, pp. 178-182.
Ridley et al., "Biomethylation of Toxic Elements in the Environment," Science, 1977, vol. 197, pp. 329-332.

* cited by examiner

*Primary Examiner* — Yun Qian
(74) *Attorney, Agent, or Firm* — Hamre, Schumann, Mueller & Larson, P.C.

(57) ABSTRACT

It is an object of the present invention to provide a beneficial composition in order to detoxify the harmful compound containing arsenic etc. effectively and systematically and a method for detoxifying a harmful compound by using the composition. The composition for the alkylation according to the present invention is characterized in that the composition contains a cobalt complex. The method of detoxifying the harmful compound according to the present invention is characterized in that a harmful compound containing at least one element selected from the groups comprising arsenic, antimony and selenium is detoxified by the alkylation of the harmful compound, in the presence of the composition according to the present invention.

16 Claims, 14 Drawing Sheets

COMPOSITION FOR ALKYLATION AND METHOD FOR DETOXIFYING A HARMFUL COMPOUND BY USING THE COMPOSITION

TECHNICAL FIELD

The present invention relates to a composition for the alkylation and a method for detoxifying a harmful compound by using the composition.

BACKGROUND ART

The heavy metal material such as arsenic, antimony and selenium is widely used as an industrial material, for example, semiconductor, but the influence on the organism by being flowed it out into an environment is concerned, since it is harmful material for the organism.

In the past, as a method for treating these heavy metal, a method wherein a flocculating agent such as polychlorinated aluminum (PAC) is added into the wastewater containing an inorganic arsenic such as a harmful arsenous acid, and then the inorganic arsenic is removed by the filtration after the inorganic arsenic is aggregated, adsorbed to the flocculating agent and iron contained in a raw water and then precipitated, or a method wherein an arsenic compound etc. is adsorbed by using an activated alumina, cerium based flocculating agent, are generally known.

On the other hand, it is known in nature that an inorganic arsenic is stored in sea food such as a seaweed, and then a part of the inorganic arsenic is converted to an organic arsenic compound such as dimethyl arsenic by the physiological response-(Nonpatent literature 1: Kaise et al., 1998, Organomet. Chem., 12 137-143). And it is generally known that these organic arsenic compound has lower toxicity than that of the inorganic arsenic for the mammal.
Nonpatent literature 1: Kaise et al., 1998, Organomet. Chem., 12 137

DISCLOSURE OF THE INVENTION

Problems to be Resolved by the Invention

However, in the above method of removing the heavy metal characterized by the use of the filtration and adsorption, it is necessary to store or reclaim a polluted sludge containing the harmful compound such as the inorganic arsenic which is still harmful, and an absorbent to which the harmful compound is absorbed, under the condition of sealing off the harmful compound with the use of the concrete etc., in order to prevent it from being leaked to the outside. Therefore, there is problem that the mass disposal is difficult since a storage place or a large space for a reclaimed area are required.

Moreover, it is internationally recognized that an arsenic contained in the sea food is a harmless arsenobetaine, in the present invention, it is possible to attain the detoxification by chemically converting the highly toxic inorganic arsenic to the harmless arsenobetaine.

Therefore, it is an object of the present invention to provide a beneficial composition in order to detoxify the harmful compound containing arsenic etc. effectively and systematically and a method for detoxifying a harmful compound by using the composition.

Means of Solving the Problems

In order to accomplish the above objects, the present inventors made strenuous studies on the methylating reaction of the harmful compound, specifically, the methylation, especially dimethylation, and more preferably trimethylation of the harmful compound containing arsenic etc., by chemical reactions with the use of an organic metal complex having cobalt-carbon bond. As a result, the inventors discovered the present invention.

That is, the composition for the alkylation according to the present invention is characterized in that the composition contains a cobalt complex.

Furthermore, in a preferred embodiment of the composition for the alkylation according to the present invention, the composition is characterized in that the harmful compound containing at least one element selected from the groups comprising arsenic, antimony and selenium is alkylated by using the cobalt complex.

Furthermore, in a preferred embodiment of the composition for the alkylation according to the present invention, the composition is characterized by further containing a reducing agent to reduce at least one metal selected from the groups comprising arsenic, antimony and selenium.

Furthermore, in a preferred embodiment of the composition for the alkylation according to the present invention, the composition is characterized in that the reducing agent is a material having SH group.

Furthermore, in a preferred embodiment of the composition for the alkylation according to the present invention, the composition is characterized in that the material having SH group is at least one selected from the groups comprising glutathione, reduced glutathione (GSH), cysteine, S-adenosyl cysteine, sulforaphane, homocysteine and thioglycol.

Furthermore, in a preferred embodiment of the composition for the alkylation according to the present invention, the composition is characterized in that the composition further contains a methylating additive factor having S-Me group.

Furthermore, in a preferred embodiment of the composition for the alkylation according to the present invention, the composition is characterized in that the methylating additive factor is at least one selected from the groups comprising methionine and S-adenosyl methionine.

Furthermore, in a preferred embodiment of the composition for the alkylation according to the present invention, the composition is characterized in that the composition further contains a buffer solution.

Furthermore, in a preferred embodiment of the composition for the alkylation according to the present invention, the composition is characterized in that a pH of the buffer solution is in the range of 5-10.

Furthermore, in a preferred embodiment of the composition for the alkylation according to the present invention, the composition is characterized in that a pH of the composition for the alkylation is less than 9.

Furthermore, in a preferred embodiment of the composition for the alkylation according to the present invention, the composition is characterized in that the composition further contains $H_2O_2$.

Furthermore, in a preferred embodiment of the composition for the alkylation according to the present invention, the composition is characterized in that the composition further contains an organic halide compound.

Furthermore, in a preferred embodiment of the composition for the alkylation according to the present invention, the composition is characterized in that the organic halide compound is methyl halide.

Furthermore, in a preferred embodiment of the composition for the alkylation according to the present invention, the composition is characterized in that the methyl halide is at least one selected from the groups comprising methyl iodide, methyl bromide and methyl chloride.

Furthermore, in a preferred embodiment of the composition for the alkylation according to the present invention, the composition is characterized in that the organic halide compound is halogenated acetic acid.

Furthermore, in a preferred embodiment of the composition for the alkylation according to the present invention, the composition is characterized in that the halogenated acetic acid is at least one selected from the groups comprising chloroacetic acid, bromoacetic acid and iodoacetic acid.

Furthermore, in a preferred embodiment of the composition for the alkylation according to the present invention, the composition is characterized in that the organic halide compound is at least one selected from the groups comprising methyl chloride, methyl bromide, methyl iodide, chloroacetic acid, bromoacetic acid, iodoacetic acid, chloroethanol, bromoethanol, iodoethanol, chloropropionic acid, bromopropionic acid, iodopropionic acid, chloroacetic acid ethyl ester, bromoacetic acid ethyl ester and iodoacetic acid ethyl ester.

Furthermore, in a preferred embodiment of the composition for the alkylation according to the present invention, the composition is characterized in that the organic halide compound is the Grignard reagent represented by the following chemical formula 1:

RMgX   Chemical formula 1:

(wherein R=Me, $CH_2COOH$, or $CH_2COOC_2H_5$, X=Cl, Br or I).

Furthermore, in a preferred embodiment of the composition for the alkylation according to the present invention, the composition is characterized in that the organic halide compound is derived from a persistent organic material selected from the groups comprising a pesticide, a fire retardant, dioxin, PCB, DDT, trihalomethane, trichloroethyl and chloroform.

Furthermore, in a preferred embodiment of the composition for the alkylation according to the present invention, the composition is characterized in that the composition further contains a reducing agent to reduce the cobalt complex.

Furthermore, in a preferred embodiment of the composition for the alkylation according to the present invention, the composition is characterized in that the reducing agent is at least one selected from the groups comprising titanium oxide and ruthenium complex.

Furthermore, in a preferred embodiment of the composition for the alkylation according to the present invention, the composition is characterized in that the cobalt complex is methyl complex comprising at least one compound selected from methylcobalamin (methylated vitamin B12, official name: Coα-[α-5,6-dimethylbenz-1H-imidazole-1-yl-Coβ-methylcobamide]), vitamin B12 such as cyanocobalamin, cobalt(II) acetyl acetonate, cobalt(III) acetyl acetonate, cobalt carbonyl (dicobalt octacarbonyl), cobalt(II)1,1,1,5,5,5-hexafluoro acetyl acetonate, cobalt(II) meso-tetra phenyl porphin, hexafluoro phosphoric acid bis(pentamethyl cyclopenta dienyl) cobalt, N,N'-bis(salicylidene) ethylene diamine cobalt(II), bis(2,2,6,6-tetramethyl-3,5-heptanedionato)cobalt(II), (chlorophthalocyaninnato)cobalt(II), chlorotris (triphenylphosphine) cobalt(I), methyl complex of cobalt(II) acetate, cobalt(II) benzoate, cobalt(II) cyanide, cyclohexane cobalt(II) butyrate, 2-cobalt(II) ethylhexanoate, meso-tetramethoxyphenyl porphyrin cobalt(II), cobalt naphthenate, cobalt(II) phthalocyanine, methyl cobalt(III) protoporphyrin IX, cobalt stearate, cobalt(II) sulfamate, (1R,2R)-(−)-1,2-cyclohexanediamino-N,N'-bis(3,5-di-t-butylsalicylidene)cobalt(II), (1S,2S)-(+)-1,2-cyclohexanediamino-N,N'-bis(3,5-di-t-butylsalicylidene)cobalt(II), cyclopentadienyl bis (triphenylphosphine) cobalt(I), cyclopentadienyl cobalt dicarbonyl, dibromo bis(triphenylphosphine)cobalt(II), (tetraminochloro phthalocyaninnato)cobalt(II), (tetra-t-butyl phthalocyaninnato) cobalt(II), or at least one selected from the groups comprising cobalt-methyl complex formed by allowing the cobalt compound to coexist with the alkyl halide, especially methyl halide.

Furthermore, in a preferred embodiment of the composition for the alkylation according to the present invention, the composition is characterized in that a ratio between a molarity [Reducing Agent] of the reducing agent to reduce at least one metal selected from the groups comprising arsenic, antimony and selenium and a molarity [Metal] of the metal selected from arsenic, antimony and selenium, that is, a [Reducing Agent]/[Metal] is greater or equal to 1000.

Furthermore, in a preferred embodiment of the composition for the alkylation according to the present invention, the composition is characterized in that the ratio is greater or equal to 10000.

Furthermore, in a preferred embodiment of the composition for the alkylation according to the present invention, the composition is characterized in that a ratio between a molarity [Co complex] of the cobalt complex and a molarity [Metal] of the metal selected from arsenic, antimony and selenium, that is, a [Co complex]/[Metal] is greater or equal to 100.

Furthermore, in a preferred embodiment of the composition for the alkylation according to the present invention, the composition is characterized in that the ratio is greater or equal to 1000.

The method of detoxifying the harmful compound according to the present invention, the method is characterized in that a harmful compound containing at least one element selected from the groups comprising arsenic, antimony and selenium is detoxified by the alkylation of the harmful compound, in the presence of the above composition.

Furthermore, in a preferred embodiment of the method of detoxifying the harmful compound according to the present invention, the method is characterized in that the detoxification is attained by increasing the oxidation number of a valence of the one element.

Furthermore, in a preferred embodiment of the method of detoxifying the harmful compound according to the present invention, the method is characterized in that at least one bond of the one element is alkylated.

Furthermore, in a preferred embodiment of the method of detoxifying the harmful compound according to the present invention, the method is characterized in that the element is arsenic.

Furthermore, in a preferred embodiment of the method of detoxifying the harmful compound according to the present invention, the method is characterized in that 50% of a lethal dose ($LD_{50}$) of the compound detoxified by the alkylation is greater or equal to 1000 mg/kg.

Furthermore, in a preferred embodiment of the method of detoxifying the harmful compound according to the present invention, the method is characterized in that 50% of an inhibition of cell growth concentration ($IC_{50}$) of the compound detoxified by the alkylation is greater or equal to 1000 μM.

Furthermore, in a preferred embodiment of the method of detoxifying the harmful compound according to the present invention, the method is characterized in that the harmful compound is selected from the groups comprising arsenic trioxide, arsenic pentoxide, arsenic trichloride, arsenic pentachloride, arsenic sulfide compound, cyano arsenic compound, chloro arsenic compound, and the other arsenic inorganic salt.

Furthermore, in a preferred embodiment of the method of detoxifying the harmful compound according to the present invention, the method is characterized in that the alkylation is a methylation.

Furthermore, in a preferred embodiment of the method of detoxifying the harmful compound according to the present invention, the method is characterized in that the harmful compound is converted to a dimethyl compound, or trimethyl compound by the methylation.

Furthermore, in a preferred embodiment of the method of detoxifying the harmful compound according to the present invention, the method is characterized in that the dimethyl compound is dimethyl arsonyl ethanol (DMAE), dimethyl arsonyl acetate (DMAA), dimethylarsinic acid or arseno sugar.

Furthermore, in a preferred embodiment of the method of detoxifying the harmful compound according to the present invention, the method is characterized in that the trimethyl compound is arsenocholine, arsenobetaine, trimethyl arseno sugar or trimethyl arsine oxide.

Furthermore, in a preferred embodiment of the method of detoxifying the harmful compound according to the present invention, the method is characterized in that an organic halide selected from the groups comprising a pesticide, a fire retardant, dioxin, PCB, DDT, trihalomethane, trichloroethyl and chloroform is detoxified by the dehalogenation of the organic halide in the presence of the above composition.

Furthermore, in a preferred embodiment of the method of detoxifying the harmful compound according to the present invention, the method is characterized in that the organic halide selected from the groups comprising a pesticide, a fire retardant, dioxin, PCB, DDT, trihalomethane, trichloroethyl and chloroform is detoxified by the dehalogenation of the organic halide in the presence of the above composition, and then in the presence of cobalt complex obtained by the reaction, the harmful compound containing at least one element selected from the groups comprising arsenic, antimony and selenium is detoxified by the alkylation of the harmful compound.

Furthermore, in a preferred embodiment of the method of detoxifying the harmful compound according to the present invention, the method is characterized in that the method further comprises the step of exposing to the light in the presence of the reducing agent to reduce the cobalt complex.

Furthermore, in a preferred embodiment of the method of detoxifying the harmful compound according to the present invention, the method is characterized in that the reducing agent is at least one selected from the groups comprising titanium oxide and ruthenium complex.

EFFECT OF INVENTION

The present invention has an advantageous effect that it is possible to alkylate the harmful compound, in particular, the harmful compound containing arsenic, antimony and selenium etc., easily and simply. Furthermore, according to the method of the present invention, it has an advantageous effect that a large space such as storage place is not required since it is possible to detoxify the harmful compound without limit. Furthermore, according to the method of the present invention, it has an advantageous effect that the unnecessary byproduct is not generated since it does not use a biological material in itself in a viable condition. Furthermore, according to the present invention, it has an advantageous effect that it is possible to decrease the harmful inorganic arsenic even more with a simple method.

BEST MODE FOR CARRYING OUT THE INVENTION

Figure 1:
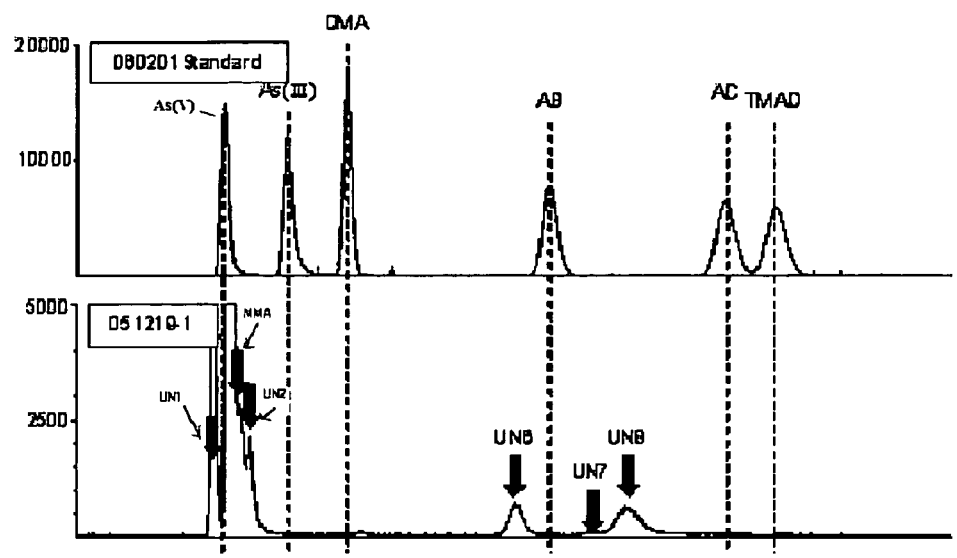
FIG. 1 gives a HPLC-ICP-MS analysis of a *chlorella* extract (Upper: standard sample, Lower: sample).

The composition for the alkylation according to the present invention contains a cobalt complex. The cobalt complex used herein is not particularly limited, but an organometallic complex having a cobalt-carbon bond etc., may be recited as an example.

As an example of the organometallic complex having a cobalt-carbon bond may be mentioned below. That is, methylcobalamin (methylated vitamin B12, official name: Coα-[α-5,6-dimethylbenz-1H-imidazole-1-yl-Coβ-methylcobamide]) is preferably used. Furthermore, mention may be made of at least one selected from the groups comprising the methyl complex of at least one compound selected from vitamin B12 such as cyanocobalamin, cobalt(II) acetyl acetonate, cobalt(III) acetyl acetonate, cobalt carbonyl (dicobalt octacarbonyl), cobalt(II)1,1,1,5,5,5-hexafluoro acetyl acetonate, cobalt(II) meso-tetra phenyl porphin, hexafluoro phosphoric acid bis(pentamethyl cyclopenta dienyl)cobalt, N,N'-bis(salicylidene) ethylene diamine cobalt(II), bis(2,2,6,6-tetramethyl-3,5-heptanedionato)cobalt(II), (chlorophthalocyaninnato) cobalt(II), chlorotris (triphenylphosphine) cobalt(I), methyl complex of cobalt(II) acetate, cobalt(II) benzoate, cobalt(II) cyanide, cyclohexane cobalt(II) butyrate, 2-cobalt(II) ethylhexanoate, meso-tetramethoxyphenyl porphyrin cobalt(II), cobalt naphthenate, cobalt(II) phthalocyanine, methyl cobalt(III) protoporphyrin IX, cobalt stearate, cobalt(II) sulfamate, (1R,2R)-(−)-1,2-cyclohexanediamino-N,N'-bis(3,5-di-t-butylsalicylidene)cobalt(II), (1S,2S)-(+)-1,2-cyclohexanediamino-N,N'-bis(3,5-di-t-butylsalicylidene)cobalt(II), cyclopentadienyl bis (triphenylphosphine) cobalt(I), cyclopentadienyl cobalt dicarbonyl, dibromo bis(triphenylphosphine)cobalt(II), (tetraminochloro phthalocyaninnato)cobalt(II), (tetra-t-butyl phthalocyaninnato)cobalt(II), or at least one selected from the groups comprising cobalt-methyl complex formed by allowing the cobalt compound to coexist with the alkyl halide, especially methyl halide. Methylcobalamin is preferable as the organometallic complex having a cobalt-carbon bond, from the viewpoint that it is possible to make it relatively easy to alkylate the harmful compound containing a harmful inorganic arsenic etc., and covert it to an organic material which has a less toxic.

That is, in the composition for the alkylation according to the present invention, it is possible to alkylate the harmful compound containing at least one element selected from the groups comprising arsenic, antimony and selenium by using the organometallic complex. The term "the harmful compound" used herein means a compound which gives any adverse affect to the organism when it is flowed out into the environment and exposed to the organism.

As a harmful compound containing arsenic among the harmful compound, mention may be made of arsenious acid, arsenic pentoxide, arsenic trichloride, arsenic pentachloride, arsenic sulfide compound, cyano arsenic compound, chloro arsenic compound, and other arsenic inorganic salt and or the like. In these arsenic, for example, $LD_{50}$ (50% of the fatal dose in mouse) is less or equal to 20, and therefore, it is generally a poisonous value for the organism.

Further, as a harmful compound containing antimony, mention may be made of antimony trioxide, antimony pentoxide, antimony trichloride, and antimony pentachloride and or the like.

Further, as a harmful compound containing selenium, mention may be made of selenium dioxide and selenium trioxide.

In a preferred embodiment, the composition of the present invention may further contain a reducing agent to reduce at least one metal selected from the groups comprising arsenic, antimony and selenium. The presence of the reducing agent makes it possible to further accelerate the alkylation. Although it is thought that a reducing ability for the arsenic or the transmethylation reaction are likely to be a rate controlling in the conversion to the arsenobetaine, it is thought that the conversion to the arsenobetaine etc., may be accelerated by adding those reducing agents. As the reducing agent like this, for example, a material having the SH group may be mentioned, which may be specifically at least one selected from the groups comprising glutathione, reduced glutathione (GSH), cysteine, S-adenosyl cysteine, sulforaphane, homocysteine and thioglycol. Moreover, any combination of these materials having the SH group may be used. For example, combinations of glutathione+homocysteine, or glutathione+thioglycol etc., may be mentioned.

Furthermore, in a preferred embodiment of the composition for the alkylation according to the present invention, a ratio between a molarity [Reducing Agent] of the reducing agent to reduce at least one metal selected from the groups comprising arsenic, antimony and selenium and a molarity [Metal] of the metal selected from arsenic, antimony and selenium, that is, a [Reducing Agent]/[Metal] is greater or equal to 1000. More preferably, the ratio is greater or equal to 10000. This is because in such conditions, it is possible to attain the alkylation in a high rate, and then to attain the detoxification of the harmful compound containing arsenic etc., effectively when the composition of the present invention is applied to the method of detoxifying the harmful compound as mentioned later.

Furthermore, in a preferred embodiment of the composition for the alkylation according to the present invention, a ratio between a molarity [Co complex] of the Co complex and a molarity [Metal] of the metal selected from arsenic, antimony and selenium, that is, a [Co complex]/[Metal] is greater or equal to 100. More preferably, the ratio is greater or equal to 1000. This is because in such conditions, it is possible to attain the alkylation in a high rate, and then to attain the detoxification of the harmful compound containing arsenic etc., effectively when the composition of the present invention is applied to the method of detoxifying the harmful compound as mentioned later.

According to the molarity ratio as mentioned above, it is possible to attain one of the primary objective of the present invention, that is, which an extremely-poisonous inorganic arsenic (Acute toxicity value: LD50 0.03 g/kg) etc., can be converted high-efficiently to a methylated arsenic etc., having a lower toxicity by the methylation of the inorganic arsenic. The methylated arsenic etc., having a lower toxicity which is an objective product are trimethylarsineoxide (Acute toxicity value: LD50 10.6 g/kg) or arsenobetaine (Acute toxicity value: LD50 10.0 g/kg) etc. It is possible to reduce a toxicity up to 1/300 compared with that of the inorganic arsenic etc., these harmless arsenic etc., can be obtained at 10% or more, preferably at 50% or more, more preferably at 90% or more at relative yield.

Furthermore, in a preferred embodiment of the composition for the alkylation according to the present invention, the composition further contains a methylating additive factor having S-Me group. The presence of the methylating additive factor having S-Me group makes it possible to produce more alkyl groups, and thereby, to attain more alkylation, and consequently more detoxification. As the methylating additive factor, mention may be made of at least one selected from the groups comprising methionine and S-adenosyl methionine.

Furthermore, the composition for the alkylation according to the present invention may further contain a buffer solution. Those generally used for the isolation, purification or preservation of the biomedical materials may be used for the buffer solution, and those are not particularly limited, but mention may be made of the buffer solution such as a tris buffer, a phosphate buffer, a carbonic acid buffer, and a boric acid buffer. Furthermore, in a viewpoint that it is possible to attain the detoxification more safely, a pH of the buffer solution is preferably in the range of 5-10. A pH of the composition for the alkylation is more preferably less than 9. The composition for the alkylation of the present invention may further contain $H_2O_2$. That is, $H_2O_2$ may be added in a viewpoint that an acute toxicity can be decreased by enhancing the oxidation state (from trivalent to pentavalent).

Furthermore, the composition for the alkylation according to the present invention may further contain an organic halide compound. In a viewpoint that it is possible to make it easy to convert a dimethyl compound and/or a trimethyl compound to arsenobetaine, methyl halide may be recited as the organic halide compound. In a viewpoint of a high reactivity of the methylation, as the methyl halide mention may be made of at least one selected from the groups comprising
methyl iodide, methyl bromide and methyl chloride.

In addition, in a viewpoint of a high reactivity of the alkylation, as the organic halide mention may be made of at least one selected from the groups comprising iodoacetic acid, iodoethanol, bromoacetic acid, bromoethanol and iodopropionic acid.

In a preferred embodiment, the organic halide is the halogenated acetic acid. As an example of the halogenated acetic acid, mention may be made of at least one selected from the groups comprising chloroacetic acid, bromoacetic acid and iodoacetic acid.

Furthermore, in a preferred embodiment, as the organic halide compound, mention may be made of at least one selected from the groups comprising methyl chloride, methyl bromide, methyl iodide, chloroacetic acid, bromoacetic acid, iodoacetic acid, chloroethanol, bromoethanol, iodoethanol, chloropropionic acid, bromopropionic acid, iodopropionic acid, chloroacetic acid ethyl ester, bromoacetic acid ethyl ester and iodoacetic acid ethyl ester.

Furthermore, in the present invention, the organic halide compound may be the Grignard reagent represented by the following chemical formula 1:

RMgX            Chemical formula 1:

(wherein R=Me, $CH_2COOH$ or $CH_2COOC_2H_5$, X=Cl, Br or I).

Moreover, the use of the organic halide compound as mentioned above is mainly explained in a viewpoint that it is possible to methylate the harmful compound, in more detail, to make it easy to convert dimethyl compound and/or trimethyl compound to stable arsenobetaine.

On the other hand, an organic halide compound as mentioned below is exemplified as those capable of being object for the detoxification by the dehalogenation in a method of detoxifying the organic halide compound according to the present invention as described later.

That is, as an organic halide compound which may be intended for the detoxification, mention may be made of those selected from the groups comprising a pesticide, a fire retardant, dioxin, PCB, DDT, trihalomethane, trichloroethyl and chloroform. In the case that these materials are not purified, these materials may be used as appropriate forms (regardless of a liquid, a gas or a solid) capable of introducing them into the reaction system in the conventional procedure such as an extraction and the separation etc. Since the cobalt complex is existed in the composition for the alkylation according to the present invention, the catalytic action of the cobalt complex makes it possible to dehalogenate the above harmful organic halide, and thereby, to detoxify the harmful organic halide by the dehalogenation.

The composition for the alkylation according to the present invention may further contain a reducing agent to reduce the cobalt complex. This has an advantageous effect that it is possible to convert the oxidation state of the cobalt complex to an active oxidation state thereof by the presence of the reducing agent, as described later.

The reducing agent like this is not particularly limited as long as it can make the cobalt complex become activated, but for example, mention may be made of at least one selected from the groups comprising titanium oxide and ruthenium complex.

Next, the method of detoxifying the harmful compound according to the present invention is explained. Namely, the method of detoxifying the harmful compound according to the present invention is characterized in that a harmful compound containing at least one element selected from the groups comprising arsenic, antimony and selenium is detoxified by the alkylation of the harmful compound, in the presence of the composition for the alkylation according to the present invention as described above. The composition for the alkylation according to the present invention, and the harmful compound used herein mean those explained above, these explanation may be applicable for the method of detoxifying the harmful compound according to the present invention.

Furthermore, in a preferred embodiment of the method of detoxifying the harmful compound according to the present invention, in the viewpoint that the 50% of an inhibition of cell growth concentration ($IC_{50}$) or the 50% of a lethal dose ($LD_{50}$) is greater, and therefore it is possible to attain more detoxification, the detoxification of the harmful compound is preferably attained by increasing the oxidation number of a valence of the one element contained in the above harmful compound. Specifically, it is possible to increase the oxidation number of a valence of the one element by the alkylation with the use of the composition of the present invention as described above as a catalyst for the reaction. Moreover, it is preferable to convert a trivalent of the oxidation number of a valence to a pentavalent in the case that the element is arsenic or antimony, and it is preferable to convert a tetravalent of the oxidation number of a valence to a hexavalent in the case of selenium.

In the present invention, the detoxification of the harmful compound is carried out by alkylating the harmful compound. At this moment, the present invention may attain the detoxification by alkylating at least one bond of the one element contained in the above harmful compound.

Specifically, it is possible to alkylate at least one bond of the one element by carrying out the reaction with the use of the composition for the alkylation of the present invention as described above. As an alkyl group added to the one element, mention may be made of a methyl group, an ethyl group, a propyl group etc. In a viewpoint that it is possible to attain the detoxification more effectively, a methyl group is preferable as an alkyl group.

In the method of detoxifying the harmful compound according to the present invention, in a viewpoint of the safety for the living organism, the 50% of a lethal dose ($LD_{50}$) (an oral toxicity which render a 50% of the fatal dose in mouse) of the compound detoxified by the above alkylation is preferably greater or equal to 1000 mg/kg, more preferably greater or equal to 5000 mg/kg.

Furthermore, in the method of detoxifying the harmful compound according to the present invention, in a viewpoint of the safety for the living organism, the 50% of an inhibition of cell growth concentration ($IC_{50}$) of the compound detoxified by the above alkylation or arylation is preferably greater or equal to 1000 μM, more preferably greater or equal to 300 μM. The term "the 50% of an inhibition of cell growth concentration ($IC_{50}$)" used herein means a numerical value which gives a necessary concentration of certain substance in order to block or inhibit a 50% of the 100 cell proliferation with the use of the substance. It shows that the smaller the numerical value of $IC_{50}$, the larger the cytotoxicity. Moreover, $IC_{50}$ was calculated from a result of the examination of the cytotoxicity which gives a plasmid DNA damage under the condition at 37° C., for 24 hours.

At this moment, $IC_{50}$ of each arsenic compound is shown in table 1

TABLE 1

| $IC_{50}$ value (μM) | | | |
|---|---|---|---|
| Arsenic(III) compound | | Arsenic(V) compound | |
| Arsenious acid | 10 | Arsenic acid | 100 |
| MMA(III) | 1 | MMA(V) | >6000 |
| DMA(III) | 1 | DMA(V) | 3000 |
| | | TMAO | >6000 |
| Arseno sugar(III) | 500 | Arseno sugar(V) | >6000 |

24 h, 37° C.

From the table 1, it is revealed that arseno sugar(III) having a trivalent arsenic(III) has higher cytotoxicity than those of monomethylated arsenic (MMA) and dimethylated arsenic (DMA) having a pentavalent arsenic, but has lower cytotoxicity than those of monomethylated arsenic (MMA), dimethylated arsenic (DMA) having a trivalent, and arsenious acid. On the other hand, it is recognized that monomethylated arsenic (MMA), dimethylated arsenic (DMA) having a trivalent arsenic has higher cytotoxicity than that of arsenious acid (trivalent and pentavalen), but as a whole, the arsenic(V) compound having a pentavalent arsenic has higher safety for the living organism than that of the arsenic(III) compound having a trivalent arsenic in a viewpoint of the cytotoxicity.

Moreover, $LD_{50}$ of each arsenic compound is shown in table 2

TABLE 2

| | Chemical species of the arsenic | $LD_{50}$ (mg/kg) |
|---|---|---|
| As(III) | Inorganic arsenic(III(valency)) | 4.5 |
| As(V) | inorganic arsenic(V(valency)) | 14-18 |
| MMA | monomethyl arsonic acid | 1,800 |
| DMA | dimethylarsinic acid | 1,200 |
| AC | arsenocholine | 6,000 |
| TMAO | trimethylarsineoxide | 10,600 |
| AB | arsenobetaine | 10,000 |

Furthermore, in the method of detoxifying the harmful compound according to the present invention, a biological half-life of the compound detoxified by the above alkylation is preferably less or equal to 8 hours in a viewpoint of the safety for the living organism. In the method of detoxifying the harmful compound according to the present invention, it is preferable to convert the harmful compound to the dimethyl compound or the trimethyl compound by means of the methylation in a viewpoint that they are safer and has a lower toxicity. As the dimethyl compound mention may be made of dimethyl arsonyl ethanol (DMAE), dimethyl arsonyl acetate (DMAA), dimethylarsinic acid or arseno sugar. As the trimethyl compound mention may be made of arsenocholine, arsenobetaine, trimethyl arseno sugar or trimethyl arsine oxide.

Furthermore, in a preferred embodiment of the method of detoxifying the harmful compound according to the present invention, the method is characterized that the organic halide selected from the groups comprising a pesticide, a fire retardant, dioxin, PCB, DDT, trihalomethane, trichloroethyl and chloroform is detoxified by the dehalogenation of the organic halide in the presence of the composition according to the present invention as mentioned above.

Furthermore, in a preferred embodiment of the method of detoxifying the harmful compound according to the present invention, it is possible to detoxify the organic halide selected from the groups comprising a pesticide, a fire retardant, dioxin, PCB, DDT, trihalomethane, trichloroethyl and chloroform by the dehalogenation of the organic halide in the presence of the composition according to the present invention as mentioned above, and then to detoxify the harmful compound containing at least one element selected from the groups comprising arsenic, antimony and selenium by the alkylation thereof in the presence of cobalt complex obtained by the reaction.

That is, if an inherently harmful organic halide, such as a pesticide, a fire retardant, dioxin, PCB, DDT, trihalomethane, trichloroethyl and chloroform is reacted in the presence of the composition for the alkylation according to the invention, the dehalogenation of the organic halide comes about, whereas an organic cobalt complex is also came about by the reaction, as a result, an organic material in the organic cobalt complex may be one of the resource of the alkyl groups for the alkylation of the harmful heavy metal. In other words, it is possible to convert the harmful compound such as the inorganic arsenic to harmless substances, that is, the organic arsenic, with the use of the resource of the alkyl groups thus obtained.

Furthermore, in a preferred embodiment of the method of detoxifying the harmful compound according to the present invention, the method further comprises the step of exposing to the light in the presence of the reducing agent to reduce the cobalt complex. The exposure to the light makes it possible to convert the cobalt(II) complex to a cobalt(I) complex with an active oxidation state. The cobalt complex(I) has an advantageous effect that the organic halide compound is detoxified by the dehalogenation by reacting the complex with the harmful organic halide compound to be dehalogenated, whereas the organic material may be also obtained which may become the resource of the alkyl groups.

The reducing agent like this, is not particularly limited as long as it can make the cobalt complex active, but for example, mention may be made of at least one selected from the groups comprising titanium oxide and ruthenium complex.

Next, the explanation of the method of detoxifying the organic halide according to the present invention is as follows.

That is, the method of detoxifying the organic halide according to the present invention is characterized in that an organic halide selected from the groups comprising a pesticide, a fire. retardant, dioxin, PCB, DDT, trihalomethane, trichloroethyl and chloroform is detoxified by the dehalogenation of the organic halide in the presence of the composition according to the present invention as described above. In the case that the organic halide selected from the groups comprising a pesticide, a fire retardant, dioxin, PCB, DDT, trihalomethane, trichloroethyl and chloroform is some forms which can not be introduced into the reaction system, these materials may be used as appropriate forms (regardless of a liquid, a gas or a solid) capable of introducing them into the reaction system according to the conventional procedure such as an extraction, the separation and purification etc. According to the present method, cobalt complex in the composition of the present invention makes a contribution to the alkylation as well as the dehalogenation of the organic halide, and then makes it possible to attain the detoxification of the organic halide. As just described, the composition of the present invention is extremely valuable. As is the case with the method of detoxifying the harmful compound of the present invention as described above, the composition may be exposed to the light in the presence of the reducing agent to reduce the cobalt complex. The explanation of the method of detoxifying the harmful compound may be also directly applicable for an explanation about the reducing agent etc., used in the method of detoxifying the organic halide.

Figure 30:
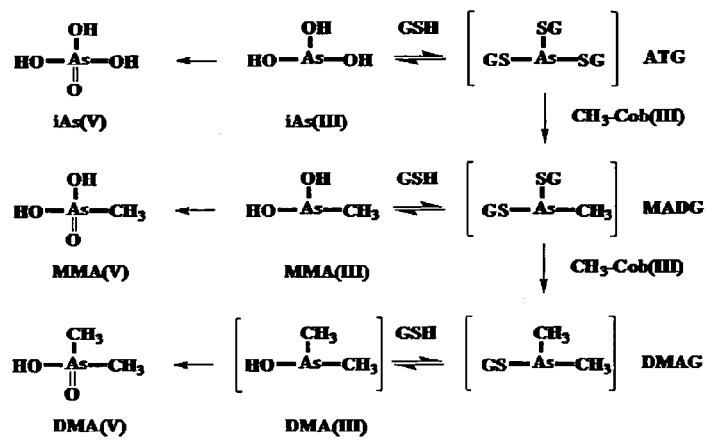
FIG. 30 shows a mechanism concerning the methylation of arsenic trioxide in the case of vitamin B12 as an example.

Moreover, FIG. 30 shows a mechanism concerning the methylation of arsenic trioxide in the case of vitamin B12 (methylcobalamin: $CH_3$-Cob(III)) as an example. In the FIG. 30, iAs(V), iAs(III), ATG, MADG and DMAG stand for pentavalent inorganic arsenic, trivalent inorganic arsenic, triglutathione arsenic complex, monomethyldiglutathione arsenic complex and dimethyl glutathione arsenic complex, respectively.

EXAMPLE

The present invention will be concretely explained in more detail with reference to Examples, but the invention is not intended to be interpreted as being limited to Examples.

At first, the explanation concerning the brevity code used in the Example is as follows:

<Brevity Code>
iAs(III): Trivalent inorganic arsenic
MMA: Monomethylated arsenic acid
DMA: Dimethylated arsinic acid
TMAO: Trimethylarsineoxide
AB: Arsenobetaine (Trimethyl arsonium acetic acid)
DMAA: Dimethyl arsonium acetic acid
MeCo: Methylcobalamin
GSH: Glutathione (Reduced form)
iSe(IV): Inorganic selenium (Tetravalent)
MIAA: Monoiodoacetic acid Example 1

<Reaction scheme>

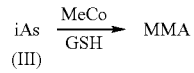

<Reacting Operation>

Into a 1.5 mL of Eppendorf tube 740 μL of a reaction buffer solution (20 mM Tris-HCl (pH7.6)) was added. To this was added 220 μL of 100 mM GSH aqueous solution, stirred for 30 seconds with Voltex, and then allowed at 37° C. for 30 minutes. To this was added 20 μL of 100 ppm inorganic arsenic (III) standard solution (for the atomic absorption) and stirred for 30 seconds. To this was added 20 μL of 7.4 mM methylcobalamin (MeCo) aqueous solution (composition A). This was reacted in a constant temperature bath maintained at 37° C., the increasing amount of the product obtained with sampling at regular intervals was examined.

<Analysis of the Product>

The qualitative and quantitative analysis was carried out by using the inductively-coupled plasma ion mass spectroscope (Agilent 7500 ce) directly connected to the high-performance liquid chromatography (Agilent 1100) online with the retention time of the standard sample compared with that of the reaction product.

Example 2

<Reaction scheme>

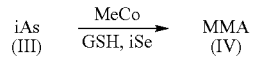

<Reacting Operation>

The experiment was carried out in the same manner as in Example 1, except that 20 μL of 1000 ppm inorganic Se (IV) standard solution (for the atomic absorption) was added to the composition A of Example 1 (Composition B).

Comparative Example 1

The experiment was carried out in the same manner as in Example 1, except for no addition of MeCo in Example 1 (Composition C). The table 3 shows a detoxification of the inorganic arsenic to MMA (Example 1) and DMA (Example 2).

TABLE 3

|  | reaction time (h) | As (V) ppm | As (III) ppm | MMA ppm | DMA ppm | Total ppm |
| --- | --- | --- | --- | --- | --- | --- |
| comparative exa. | 77 | 0.002 | 1.073 | — | — | 1.074 |
| example 1-1 | 2 | 0.002 | 1.242 | 0.002 | — | 1.246 |
| example 1-2 | 7 | 0.003 | 1.048 | 0.005 | — | 1.056 |
| example 1-3 | 24 | 2.102 | 0.022 | — | — | 2.124 |
| example 2-1 | 2 | 0.002 | 1.073 | 0.001 | — | 1.075 |
| example 2-2 | 7 | 0.001 | 0.333 | 0.007 | — | 0.341 |
| example 2-3 | 24 | 1.684 | 0.037 | — | 0.006 | 1.727 |

As shown in Examples 1-2, methyl arsenic (MMA) was generated as time advances compared with the comparative example. It was confirmed that the methylation was further proceeded, as a result, dimethylated arsenic (DMA) was also generated in Example 2. The remarkable effects was confirmed that the harmful inorganic arsenic was detoxified by being converted it to methylated arsenic having a lower toxicity in the presence of MeCo.

Figure 31:
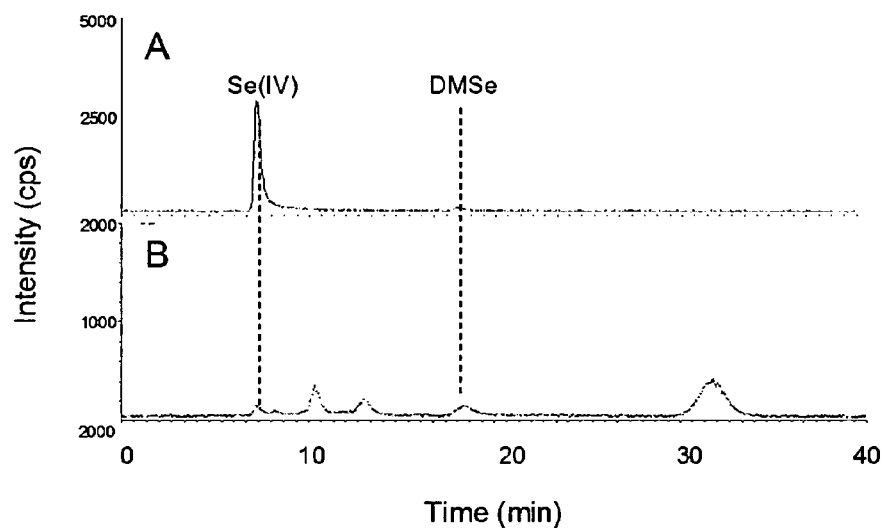
FIG. 31 gives a HPLC-ICP-MS chromatogram of the methylation reaction of selenious acid [Se(IV)] by MC.

Further, the methylation of selenium was also examined. FIG. 31 gives a HPLC-ICP-MS chromatogram of the methylation reaction of selenious acid [Se(IV)] by MC. In the Figure, A: standard sample, B: samples after the reaction, Se (IV): selenious acid and DMSe: dimethyl selenium, respectively.

As shown in FIG. 31, it was confirmed that selenious acid was converted to dimethyl selenium having a lower, toxicity.

Example 3

<Reaction scheme>

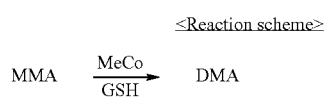

<Reacting Operation>

The experiment was carried out in the same manner as in Example 2, except that 20 μL of 1000 ppm MMA was added to the composition B of Example 2 (Composition D).

Comparative Example 2

The experiment was carried out in the same manner as in Example 3, except for no addition of MeCo in Example 3.

Example 4

<Reaction scheme>

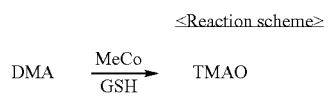

<Reacting Operation>

The experiment was carried out in the same manner as in Example 2, except that 20 μL of 1000 ppm DMA was added to the composition B of Example 2 (Composition E).

Comparative Example 3

The experiment was carried out in the same manner as in Example 4, except for no addition of MeCo in Example 4. The table 4 shows a detoxification of MMA to DMA (Example 3) and a detoxification of DMA to TMAO (Example 4).

As shown in Examples 3-1 to 3-3, the concentration of dimethyl arsenic (DMA) increased as time advances. The generation of DMA was not observed in the comparative example 2. As shown in Examples 4-1 to 4-3, the concentration of trimethyl arsenic (TMAO) increased, it was revealed that an arsenic substrate was converted to the most harmless trimethyl arsenic. The generation of trimethyl arsenic was not observed in the comparative example 3.

Example 5

<Reaction scheme>

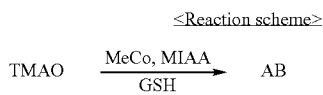

<Reacting Operation>

The experiment was carried out in the same manner as in Example 2, except that 20 μL of 1000 ppm TMAO instead of inorganic arsenic was added to the composition B of Example 2 (Composition F).

Example 6

<Reaction scheme>

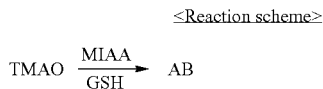

<Reacting Operation>

The experiment was carried out in the same manner as in Example 5, except for no addition of MeCo in the composition F of Example 5 (Composition G).

Example 7

<Reaction scheme>

<Reacting Operation>

The experiment was carried out in the same manner as in Example 5, except for the use of DMA instead of TMAO in the composition F of Example 5 (Composition H). Table 5 shows a conversion to arsenobetaine.

TABLE 4

|  | reaction time (h) | As (V) (ppm) | As (III) (ppm) | MMA (ppm) | DMA (ppm) | TMAO (ppm) | Total (ppm) |
| --- | --- | --- | --- | --- | --- | --- | --- |
| comparative example 2 | 2 | — | 0.010 | 14.315 | — | — | 14.325 |
| example 3-1 | 2 | — | 0.010 | 14.304 | 0.011 | — | 14.324 |
| example 3-2 | 7 | — | 2.054 | 1.651 | 0.054 | — | 3.759 |
| example 3-3 | 22 | 0.507 | 1.374 | 4.748 | 0.125 | — | 6.753 |
| comparative example 3 | 2 | — | 0.006 | 0.007 | 9.014 | — | 9.028 |
| example 4-1 | 2 | — | 0.006 | 0.007 | 9.008 | 0.006 | 9.028 |
| example 4-2 | 7 | — | 0.029 | 0.009 | 2.243 | 0.019 | 2.300 |
| example 4-3 | 22 | 0.879 | 0.297 | — | 5.104 | 0.020 | 6.300 |

TABLE 5

| | reaction time (h) | DMA (ppm) | DMAA (ppm) | TMAO (ppm) | AB (ppm) | Total (ppm) |
|---|---|---|---|---|---|---|
| example 5-1 | 2 | 0.005 | — | 13.956 | 1.183 | 15.144 |
| example 5-2 | 8 | 0.004 | — | 8.889 | 1.655 | 10.548 |
| example 5-3 | 22 | 0.005 | — | 8.716 | 1.680 | 10.401 |
| example 6-1 | 2 | 0.004 | — | 18.536 | 1.698 | 20.238 |
| example 6-2 | 8 | 0.007 | — | 17.814 | 2.530 | 20.351 |
| example 6-3 | 22 | 0.007 | — | 16.881 | 2.438 | 19.326 |
| example 6-4 | 94 | 0.013 | — | 17.424 | 2.607 | 20.044 |
| example 7-1 | 2 | 12.771 | 0.015 | 0.012 | — | 12.798 |
| example 7-2 | 22 | 17.141 | 0.434 | 0.018 | 0.007 | 18.200 |
| example 7-3 | 94 | 10.847 | 0.230 | 0.015 | 0.017 | 11.109 |

As shown in Example 5, the conversion of TMAO which is one of the arsenic substrate to AB under the presence of both MeCo and MIAA was confirmed. As shown in Example 6, the conversion of TMAO to AB under the presence of only MIAA was confirmed too. As shown in Example 7, the conversion of DMA which is one of the arsenic substrate to AB under the presence of both MeCo and MIAA was confirmed.

Example 8

At first, the explanation concerning the brevity code used in the following Example is as follows:
<Brevity Code>
iAs(III): Trivalent inorganic arsenic
MMA: Monomethylated arsenic acid
DMA: Dimethylated arsinic acid
TMAO: Trimethylarsineoxide
AB: Arsenobetaine (trimethyl arsonium acetic acid)
DMAA: Dimethyl arsonium acetic acid
MeCo: Methylcobalamin
GSH: Glutathione (reduced form)
MIAA: Monoiodoacetic acid
AS: Arseno sugar
iSe(IV): Inorganic selenium (tetravalent)
(1) Culture of the Microalgae
The microalgae, chlorella (Chlorella vulgaris IAM C-629 strain) cultivated in advance until a logarithmic growth phase was inoculated so as to obtain a 1×10$^6$ cells/mL in 150 mL Bold's Basal (BB) medium and was cultured with static culture method under exposure to the fluorescent light (4000 Lux, 24 hr illumination), at 25° C. In this case, a culture medium was prepared by adding 10 mM of glucose or 10 mM of sodium acetate as a carbon source to the culture.
(2) Accumulation Test of the Arsenic
The accumulation test of the arsenic was carried out by adding arsenous acid to the culture medium to obtain 1 ppm as a metal arsenic after the inoculation, and then culturing the microalgae for 284 hours after the addition of arsenic.
(3) Measurement of the Content of Arsenic
The qualitative and quantitative analysis concerning inorganic arsenic and organic arsenic contained in alga body was carried out by using the inductively-coupled plasma ion mass spectroscope (Agilent 7500 ce) directly connected to the high-performance liquid chromatography (Agilent 1100) online with the retention time of the standard sample compared with that of the reaction product.
(4) Condition of the Analysis
As the standard sample of the organic arsenic compound, MMA, DMA, TMAO, TeMA, AB and AC which are commercially available reagent from Optronics Co., Ltd. (Trichemical research institution) and as the standard sample of the inorganic arsenic compound, sodium salt of As(III), As(V) which are commercially available high quality reagent from Wako Pure Chemical Industries, Ltd., were used. The standard solution of 100 mg/100 mL of each arsenic compound was prepared by diluting it with an ultrapure water (Millipore).
<Condition of ICP-MS Apparatus>
RF forward power: 1.6 kW
RF reflect power: <1 W
Carrier gas flow: Ar 0.75 L/min
Sampling 8.5 mm
Monitoring mass: m/z=75 and 35 internal standard m/Z=71
Dwell time: 0.5 sec 0.01 sec 0.1 sec
Times of scan: 1 time
<Condition of H P L C>
Eluent: 5 mM nitric acid/6 mM ammonium nitrate/1.5 mM pyridine dicarboxylic acid
Flow rate of eluent: 0.4 mL/min.
Injection volume: 20 μL
Column: Cation-exchange column Shodex RSpak N,N-414 (150 mm×4.6 mm i.d.)
Column temperature: 40° C.
<Extraction of the Arsenic Compound from the Microalgae in which Arsenic is Accumulated>
A microalgae extract (wherein chlorella is treated to extract it with methanol, and then methanol is removed by the evaporation) was prepared. To this added a purified water to dilute it and to obtain a solution having a concentration described in the following table 6. Moreover, the component of an UN (Unknown) 1 and UN6 was belonged as a compound corresponding to arseno sugar (FIG. 1). FIG. 1 gives a HPLC-ICP-MS analysis of a chlorella extract (Upper: standard sample, Lower: sample). Table 6 shows a concentration (ppm) of arsenic compound of the chlorella extract.

TABLE 6

| As (V) | As (III) | MMA | DMA | UN1 | UN6 | total |
|---|---|---|---|---|---|---|
| 2.65 | 0.175 | 0.62 | 0.035 | 1.14 | 1.22 | 5.83 |

Figure 2:
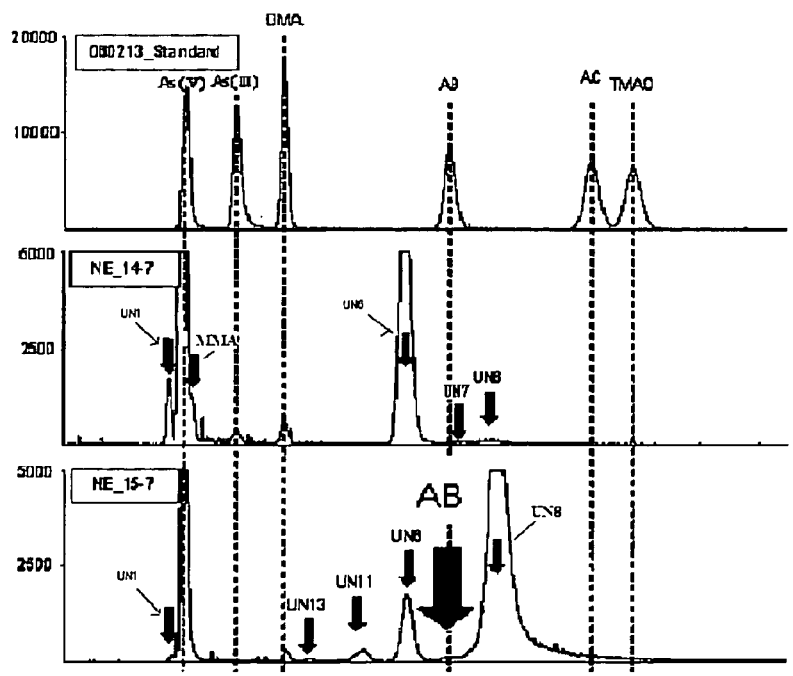
FIG. 2 gives a HPLC-ICP-MS analysis of a *chlorella* extract (Upper: standard sample, Middle: GSH addition (NE 14-7), Lower: MeCo+GSH+MIAA addition (NE 15-7)).

<Conversion to AB>
Into an Eppendorf tube with 1.5 mL volume 740 μL of a reaction buffer solution (20 mM Tris-HCl (pH7.6)) was added. To this was added 220 μL of 20 mM GSH aqueous solution, stirred with Voltex for 30 seconds, and then allowed at 37° C. for 30 minutes. To this was added 100 μL of the chlorella extract and stirred for 30 seconds. To this was added 135 μL of 7.4 mM methylcobalamin (MeCo) aqueous solution. To this was added 68 mg of MIAA (0.35 μM) to dissolve them. This was reacted in a constant temperature bath maintained at 37° C., the increasing amount of the product obtained with sampling at regular intervals was examined. As shown in FIG. 2, the generation of AB could be confirmed in the case that GSH, MeCo and MIAA are existed. FIG. 2 gives a HPLC-ICP-MS analysis of a chlorella extract (Upper: standard sample, Middle: GSH addition (NE 14-7), Lower: MeCo+GSH+MIAA addition (NE 15-7)).

Example 9

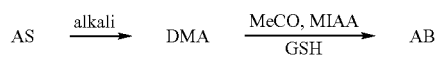

Figure 3:
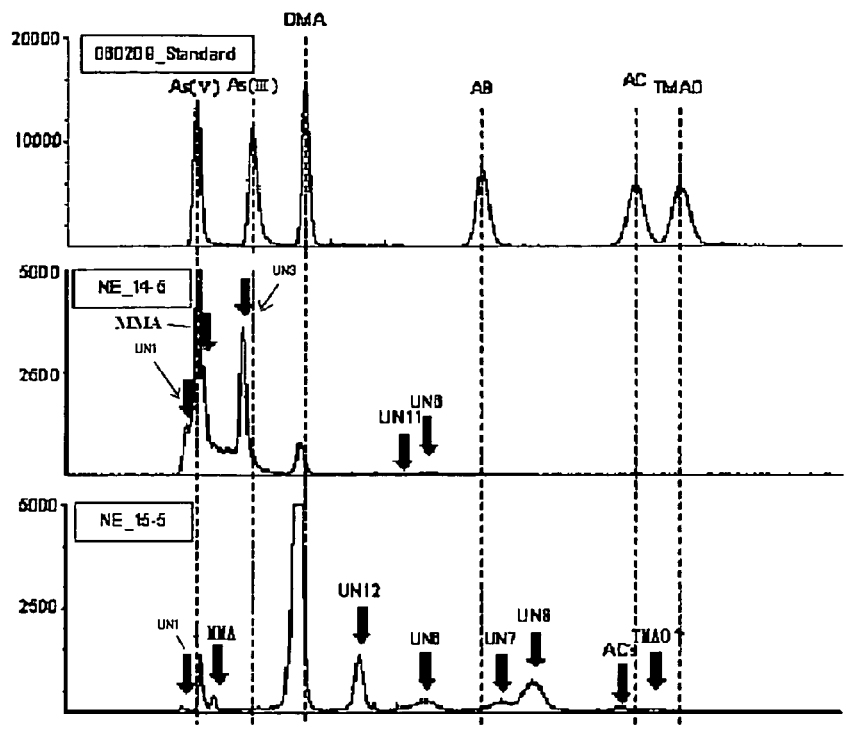
FIG. 3 shows a condition in the case that GSH (NE 14-4), GSH+MeCo +MIAA (NE 15-4) are added to the *chlorella* extract, respectively, and NaOH treatment (Lower) are subject to the *chlorella* extract.

<Conversion of Arseno Sugar to DMA>
100 μL of the chlorella extract was mixed with 4N of NaOH aqueous solution (1 mL), and allowed at 80° C. over-night. The conversion of arseno sugar to DMA was confirmed since DMA was generated(FIG. 3).

<Conversion of DMA to AB>

Figure 4:
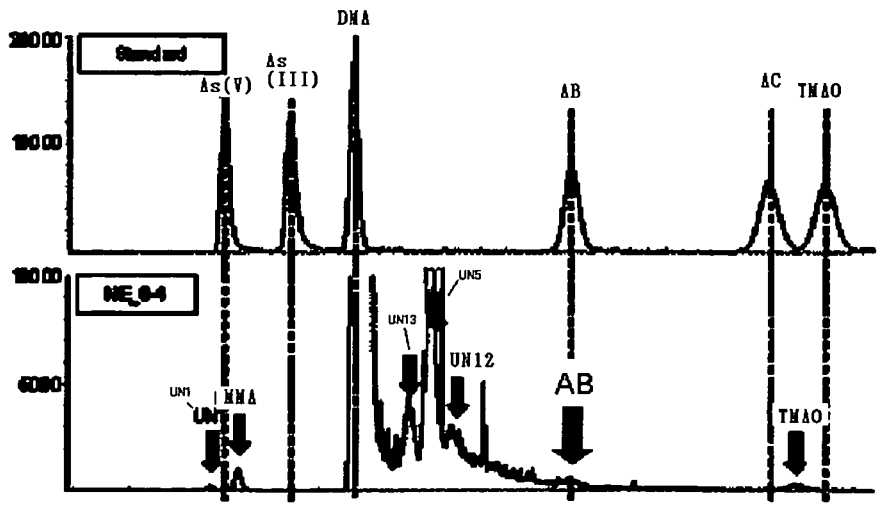
FIG. 4 shows a condition in the case that GSH+MeCo+ MIAA are added to DMA (NE 9-4).

The experiment was carried out in the same manner as in Examples 1-7. FIG. 3 shows a condition in the case that GSH (NE 14-4), GSH+MeCo+MIAA (NE 15-4) are added to the *chlorella* extract, respectively, and NaOH treatment (lower) are subject to the *chlorella* extract. Furthermore, FIG. 4 shows a condition in the case that GSH+MeCo +MIAA are added to DMA (NE 9-4).

Example 10

Further, the experiment was carried out by using methylcobalamin as a cobalt complex. At first, into a 1.5 mL of Eppendorf tube 10 mg of methylcobalamin (Wako Pure Chemical Industries, Ltd.) was added. To this was added 1 mL of an ultrapure water (18 MΩ/cm) to dissolve methylcobalamin (7.4 mmol/L) (Solution A). Into a 1.5 mL of Eppendorf tube 30.7 mg of glutathione (reduced form) was added to dissolve it with 1 mL of the ultrapure water (100 mmol/L) (Solution B). Arsenous acid aqueous solution (for an atomic absorption: 100 ppm: as metal arsenic) was prepared (Solution C). Selenious acid aqueous solution (for an atomic absorption: 1000 ppm: as metal selenium) was prepared (Solution D). 100 mmol/L of Tris-HCl buffer solution (pH 7.8, 0.01 mol/L, pH was adjusted by using hydrochloric acid solution) was prepared (Solution E). Into a 1.5 mL of Eppendorf tube 720 µL of the solution E, 20 µL of the solution C, 220 µL of the solution B were added respectively, and allowed at 37° C. for 1 hour. To this were added 20 µL of the solution A and 20 µL of the solution D, and then reacted in a constant temperature bath maintained at 37° C. The condition of the reaction is as follows:

<Condition of the Reaction>

Concentration of the substrate: [As]=30 µmmol/L

Concentration of native vitamin B12 (methylcobalamin): [MeCo]=150 µmol/L

Concentration of glutathione (reduced form): [GSH]=22 mmol/L

Concentration of selenium: [Se]=760 µmol/L

Buffer solution: 100 mMTris-HCl buffer solution (pH7.8), reaction temperature: 37° C., reaction solution: pH 3

A qualitative and quantitative analysis was carried out by using a HPLC-ICP-MS method at regular time intervals with sampling 50 mL to dilute it by ten times with the ultrapure water (No. 1-8 of the table 7).

TABLE 7

| No. | Time (hr) | As (V) | MMA | MMA (III) | As (III) | DMA | Total |
|---|---|---|---|---|---|---|---|
| 1 | 0.5 | 0.173 | 0.000 | 0.000 | 26.120 | 0.000 | 1.972 |
| 2 | 1 | 0.163 | 1.171 | 0.213 | 23.799 | 0.075 | 1.907 |
| 3 | 2 | 0.152 | 2.305 | 0.440 | 22.651 | 0.109 | 1.924 |
| 4 | 4 | 0.156 | 2.900 | 0.915 | 21.545 | 0.129 | 1.923 |
| 5 | 21 | 0.361 | 4.383 | 0.588 | 19.311 | 0.153 | 1.860 |
| 6 | 48 | 0.712 | 4.869 | 0.000 | 17.565 | 0.187 | 1.750 |
| 7 | 72 | 0.605 | 3.621 | 0.000 | 12.469 | 0.160 | 1.264 |
| 8 | 360 | 2.481 | 6.659 | 0.000 | 19.316 | 0.860 | 2.199 |
| 9 | 21 | 13.609 | 6.973 | 0.000 | 0.000 | 0.165 | 1.556 |
| 10 | 48 | 13.333 | 6.741 | 0.000 | 0.000 | 0.224 | 1.522 |

TABLE 7-continued

| No. | Time (hr) | As (V) | MMA | MMA (III) | As (III) | DMA | Total |
|---|---|---|---|---|---|---|---|
| 11 | 12 | 9.477 | 4.099 | 0.000 | 0.000 | 0.176 | 1.031 |
| 12 | 360 | 19.261 | 8.264 | 0.000 | 0.000 | 0.873 | 2.130 |

Figure 5:
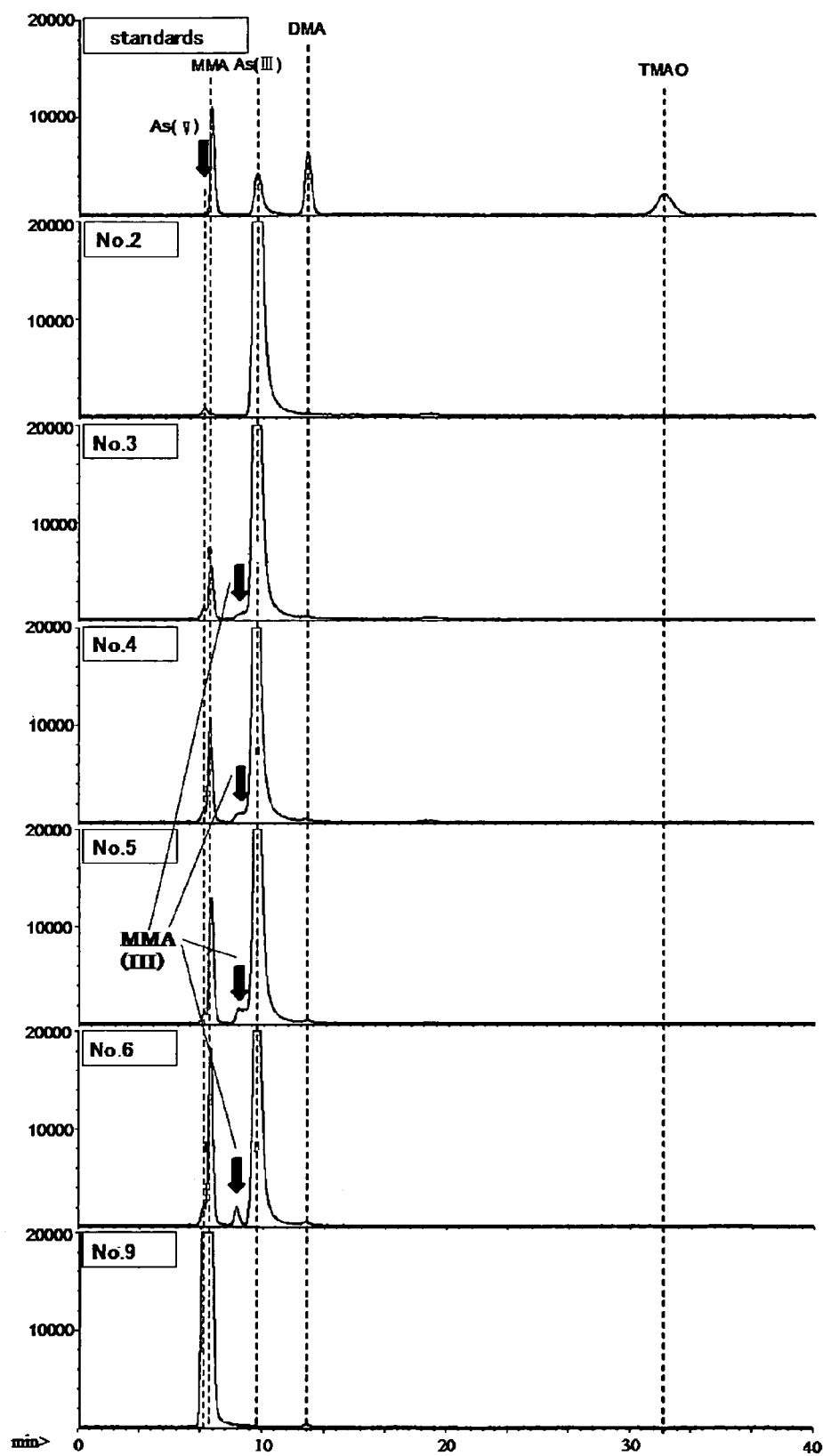
FIG. 5 gives a HPLC-ICP-MS chromatogram. A No. on the graph corresponds to a No. on the table 7.
Figure 6:
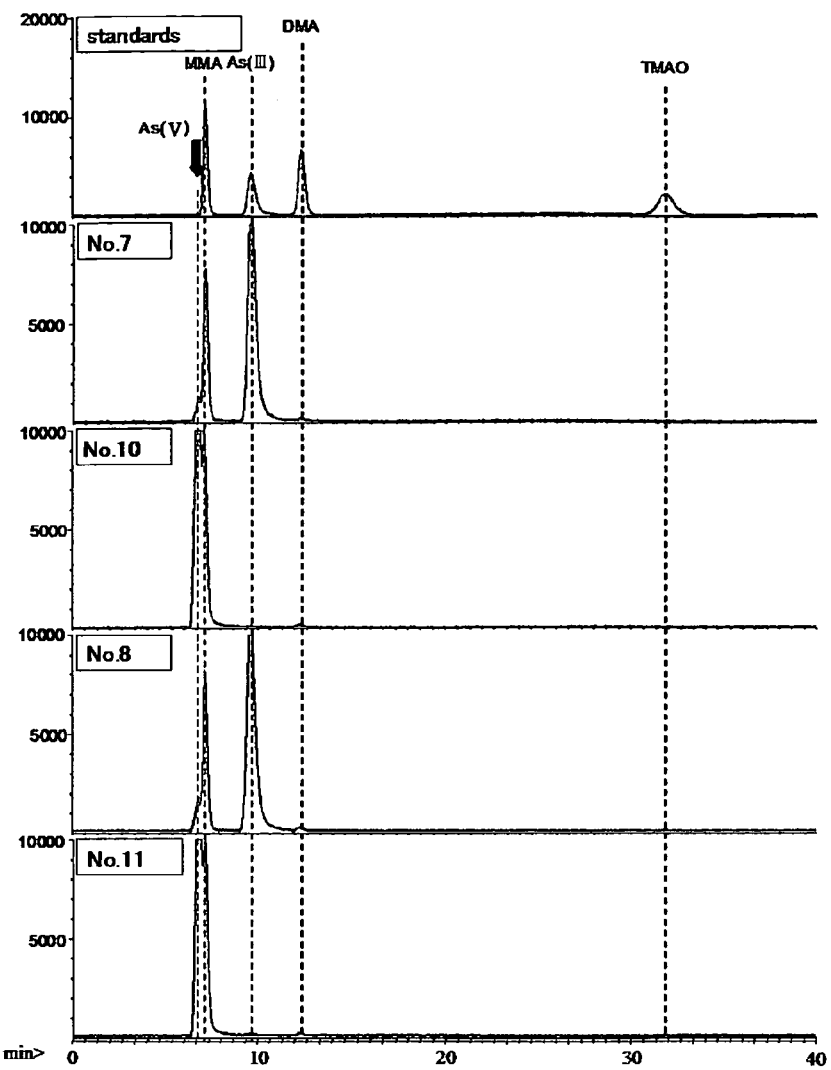
FIG. 6 gives a HPLC-ICP-MS chromatogram. A No. on the graph corresponds to a No. on the table 7.
Figure 7:
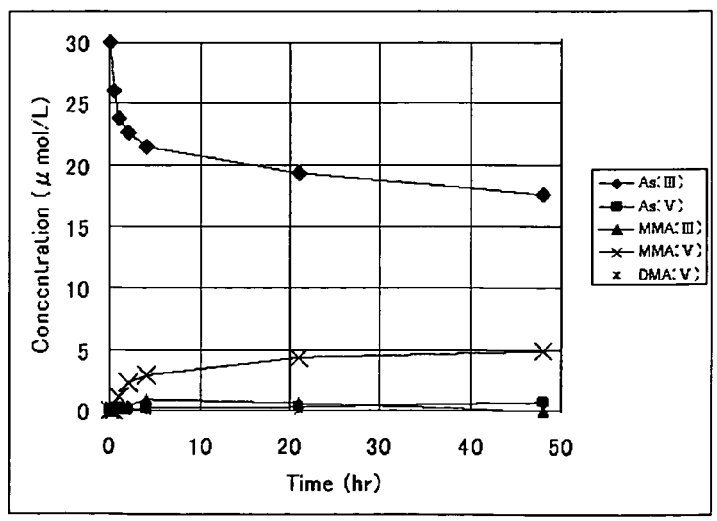
FIG. 7 shows a variation per hour of the concentration of an arsenic compound in the reaction solution. It is in a graph form as to the result of the table 7.
Figure 8:
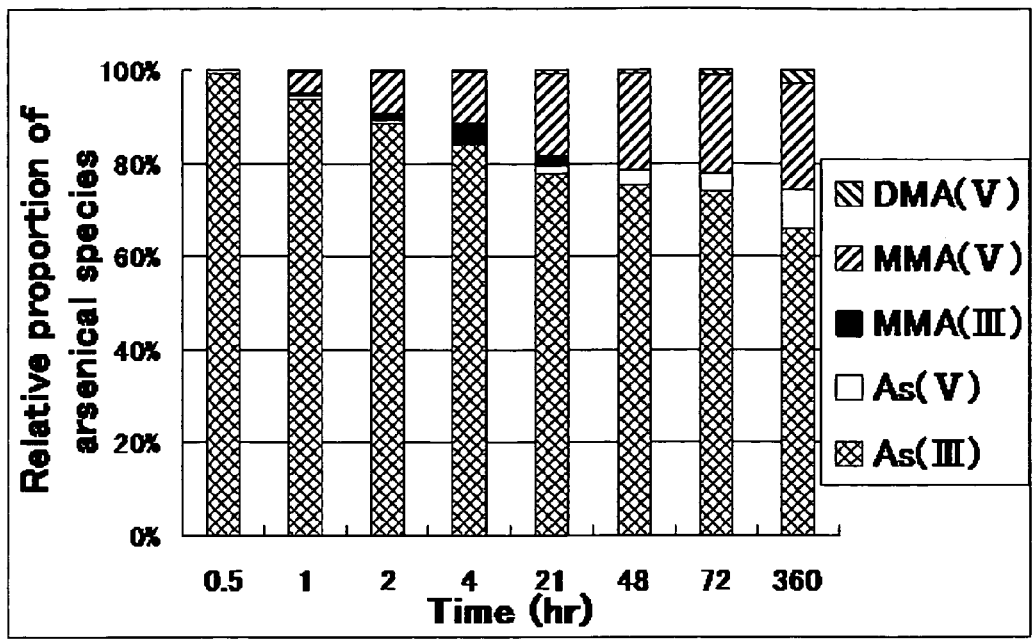
FIG. 8 shows a variation per hour of the percentage of an arsenic compound in the reaction solution.
Figure 9:
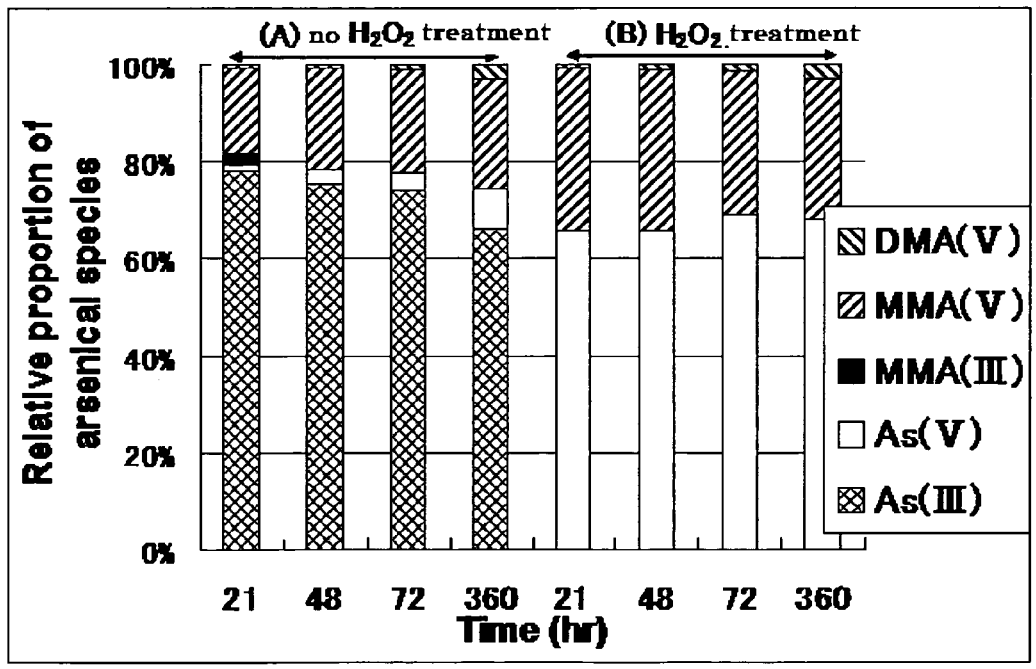
FIG. 9 shows a variation per hour of the percentage an arsenic compound in the reaction solution.
Figure 10:
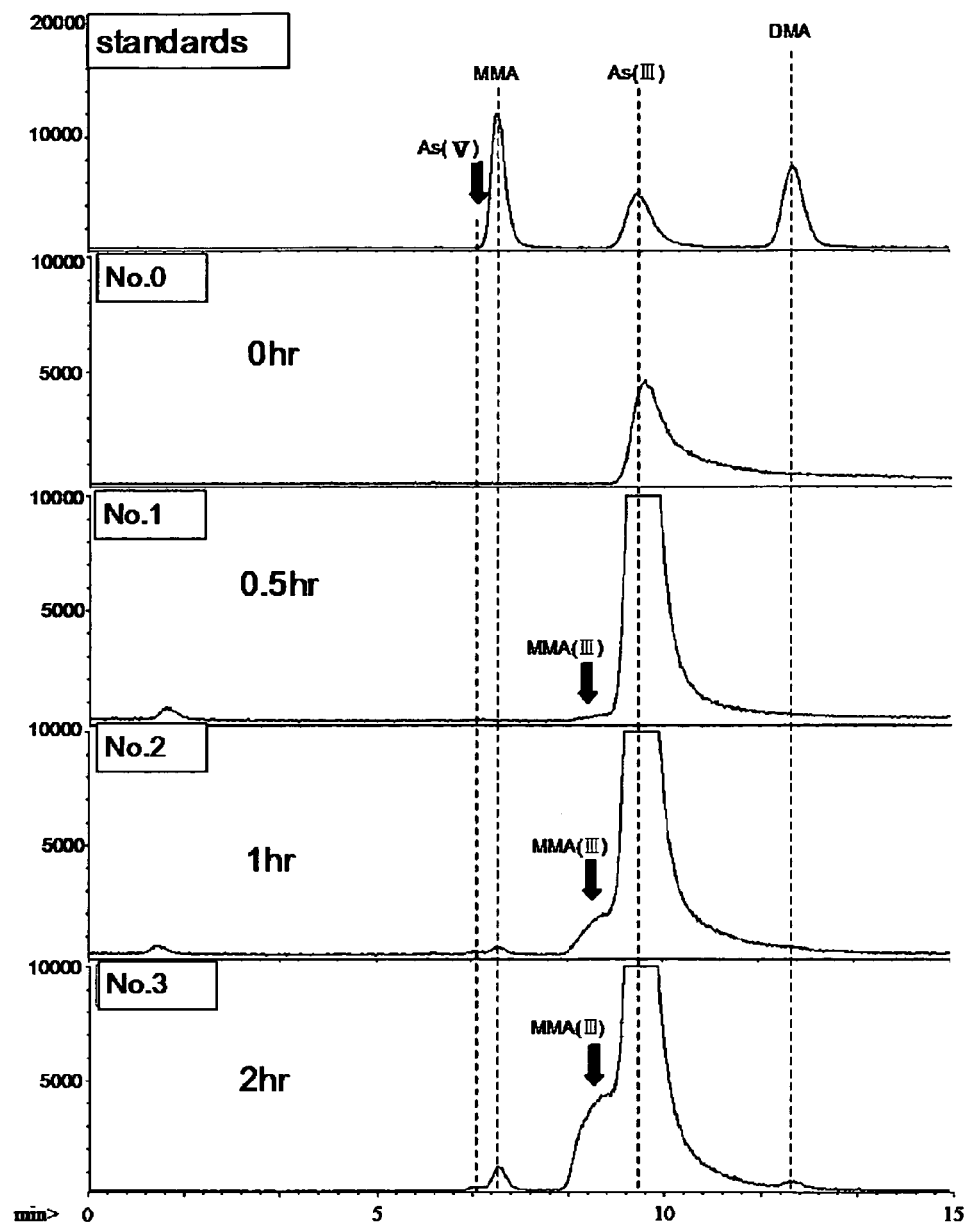
FIG. 10 gives a HPLC-ICP-MS chromatogram. A No. on the graph corresponds to a No. on the table 8.
Figure 11:
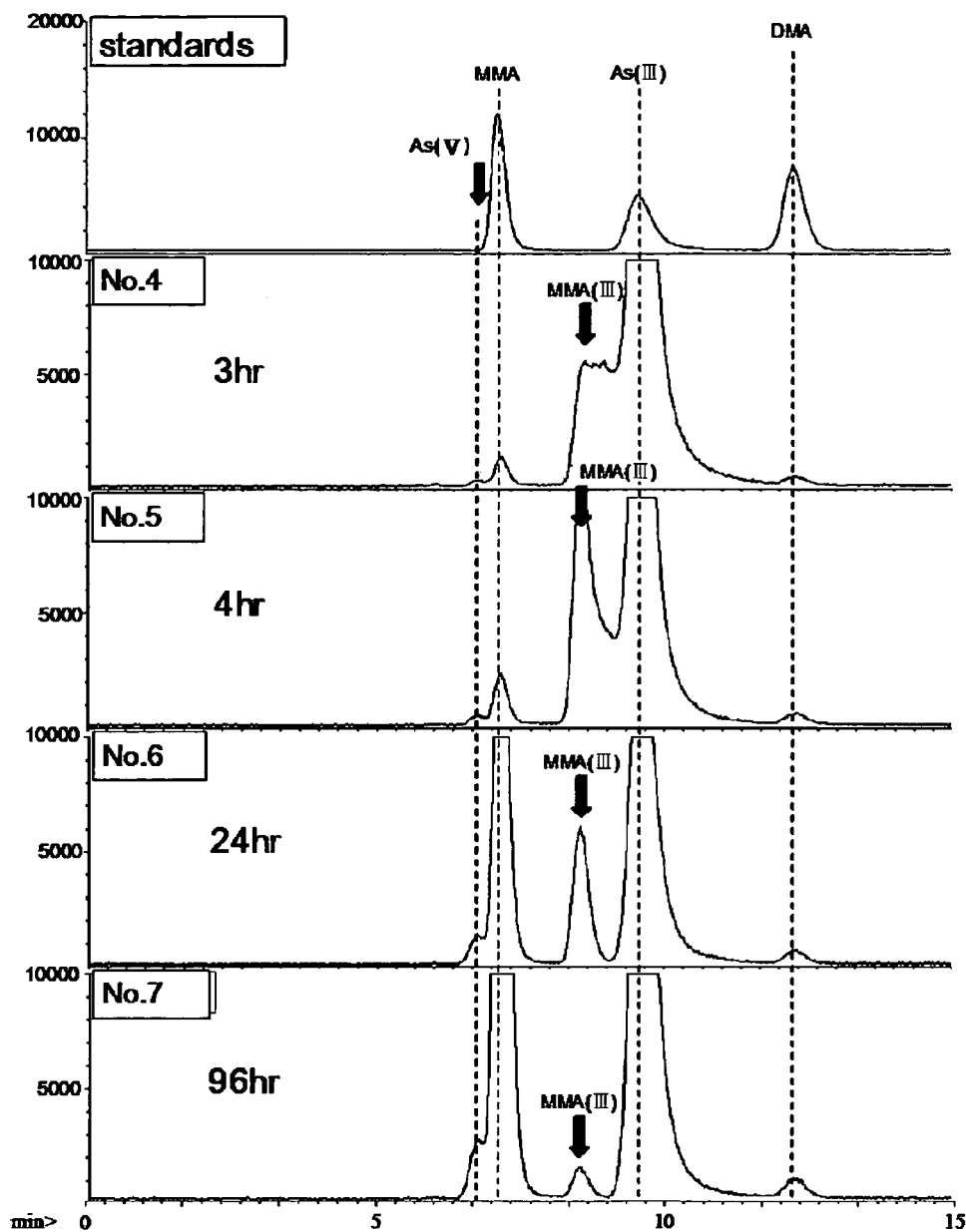
FIG. 11 gives a HPLC-ICP-MS chromatogram. A No. on the graph corresponds to a No. on the table 8.
Figure 12:
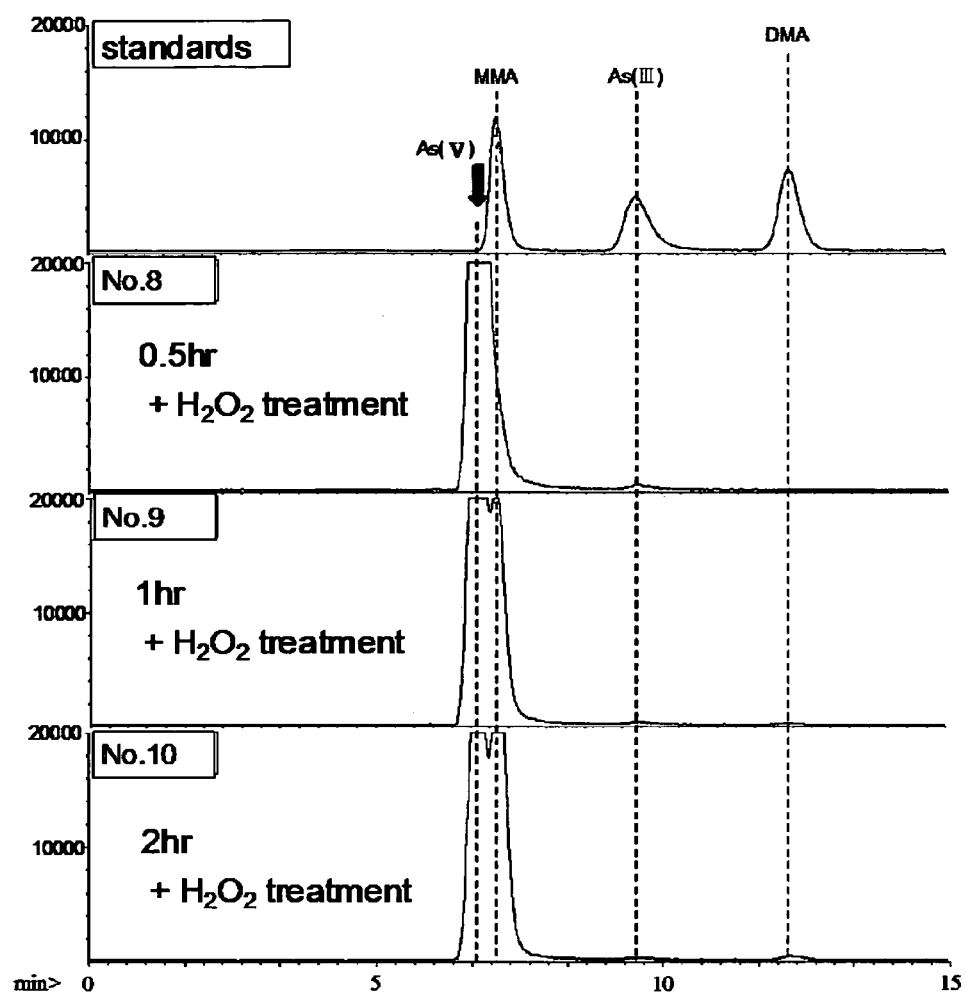
FIG. 12 gives a HPLC-ICP-MS chromatogram. A No. on the graph corresponds to a No. on the table 8.
Figure 13:
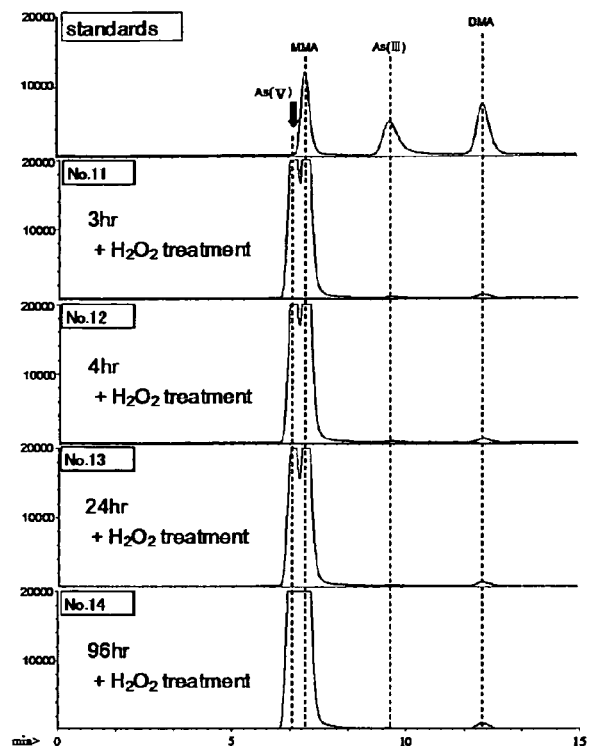
FIG. 13 gives a HPLC-ICP-MS chromatogram. A No. on the graph corresponds to a No. on the table 8.
Figure 14:
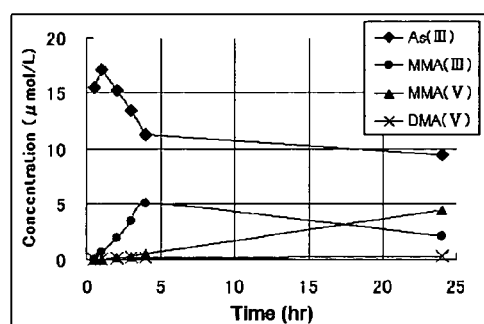
FIG. 14 shows a variation per hour of the concentration of an arsenic compound in the reaction solution.
Figure 15:
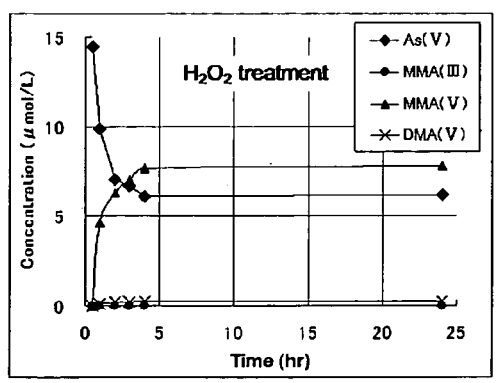
FIG. 15 shows a variation per hour of the concentration of an arsenic compound in the reaction solution (After hydrogen peroxide solution treatment).
Figure 16:
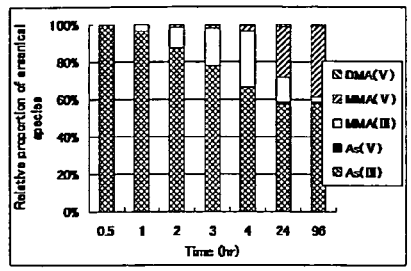
FIG. 16 shows a variation per hour of the percentage of an arsenic compound in the reaction solution (Before hydrogen peroxide treatment).
Figure 17:
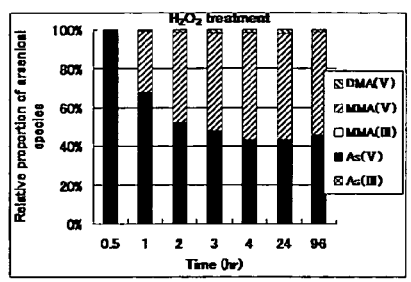
FIG. 17 shows a variation per hour of the percentage of an arsenic compound in the reaction solution (After hydrogen peroxide treatment).
Figure 18:
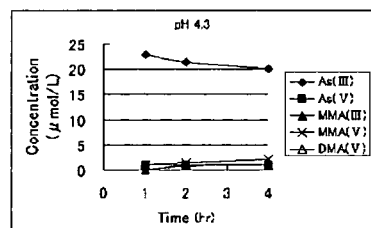
FIG. 18 shows a variation per hour of the concentration of an arsenic compound in the reaction solution (No. 1-4 of the table 9).
Figure 19:
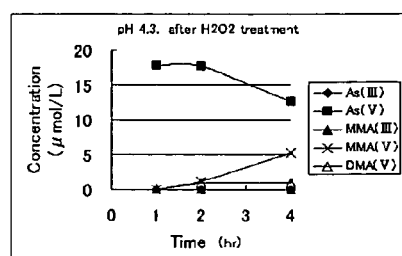
FIG. 19 shows a variation per hour of the concentration of an arsenic compound in the reaction solution (No. 5-8 of the table 9, after hydrogen peroxide solution treatment).
Figure 20:
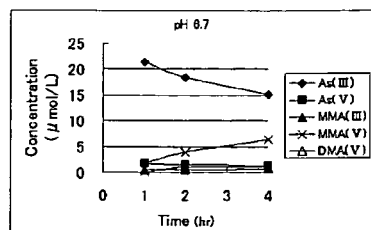
FIG. 20 shows a variation per hour of the concentration of an arsenic compound in the reaction solution (No. 9-12 of the table 9).
Figure 21:
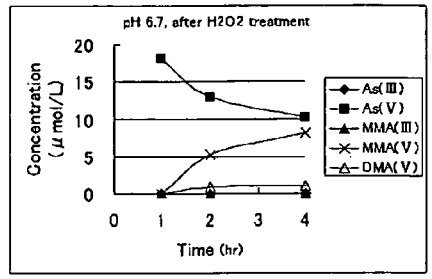
FIG. 21 shows a variation per hour of the concentration of an arsenic compound in the reaction solution (No. 13-16 of the table 9, after hydrogen peroxide solution treatment).
Figure 22:
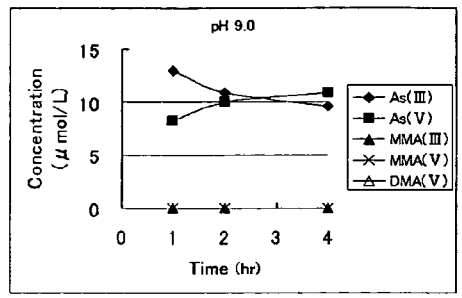
FIG. 22 shows a variation per hour of the concentration of an arsenic compound in the reaction solution (No. 17-20 of the table 9, before hydrogen peroxide solution treatment).
Figure 23:
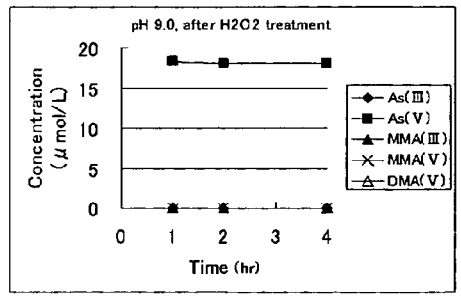
FIG. 23 shows a variation per hour of the concentration of an arsenic compound in the reaction solution (No. 21-24 of the table 9, before hydrogen peroxide solution treatment).
Figure 24:
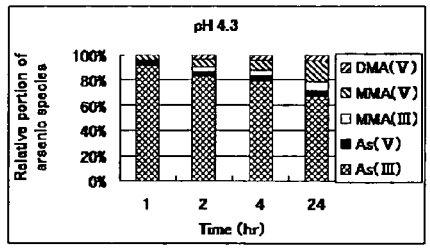
FIG. 24 shows a variation per hour of the percentage of an arsenic compound in the reaction solution (No. 1-4 of the table 9, before hydrogen peroxide treatment).
Figure 25:
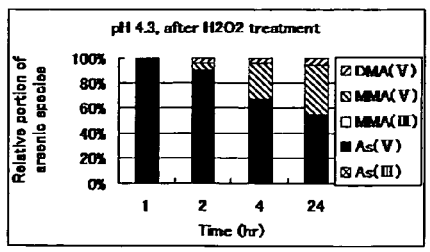
FIG. 25 shows a variation per hour of the percentage of an arsenic compound in the reaction solution (No. 5-8 of the table 9, after hydrogen peroxide solution treatment).
Figure 26:
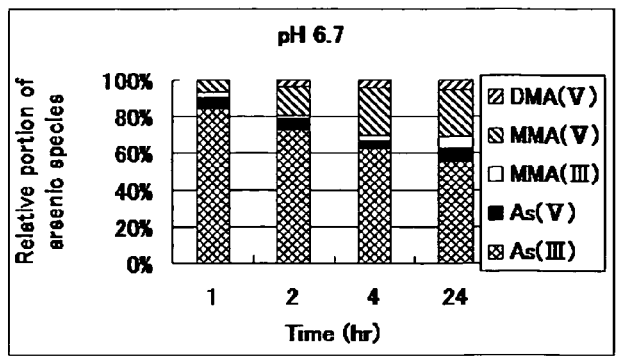
FIG. 26 shows a variation per hour of the percentage of an arsenic compound in the reaction solution (No. 9-12 of the table 9, before hydrogen peroxide solution treatment).
Figure 27:
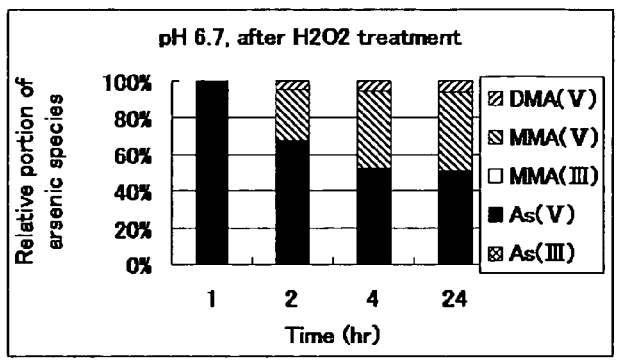
FIG. 27 shows a variation per hour of the percentage of an arsenic compound in the reaction solution (No. 13-16 of the table 9, after hydrogen peroxide solution treatment).
Figure 28:
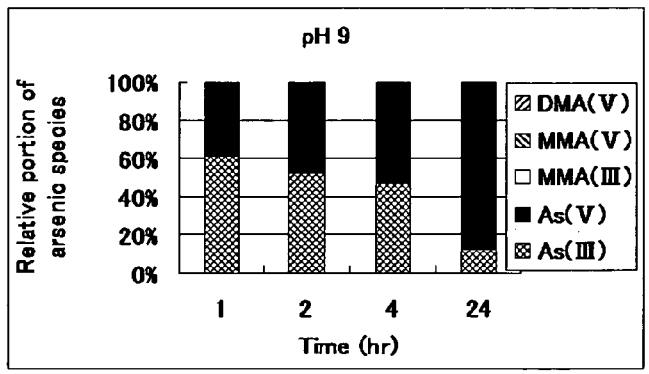
FIG. 28 shows a variation per hour of the percentage of an arsenic compound in the reaction solution (No. 17-20 of the table 9, before hydrogen peroxide solution treatment).
Figure 29:
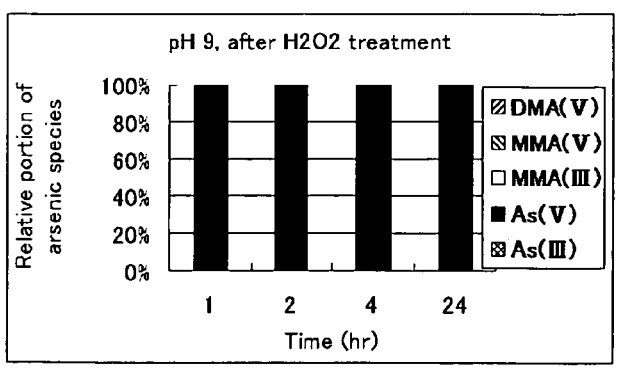
FIG. 29 shows a variation per hour of the percentage of an arsenic compound in the reaction solution (No. 21-24 of the table 9, after hydrogen peroxide solution treatment).

FIG. 7 shows a variation per hour of the concentration of the arsenic compound in the reaction solution (which is in graph form of the result of the table 7). Moreover, with sampling 50 µL from the reaction solution to obtain a sample, and the obtained sample was treated with 50 mL of hydrogen peroxide solution (37° C., 1 hour) to dilute it by ten times with the ultrapure water so that the reaction product could be analyzed in a similar way (No. 9-11 of the table 7). FIGS. 5 and 6 give a HPLC-ICP-MS chromatogram.

Example 11

The experiment was carried out in the same manner as in Example 10, except that the solution B was adjusted to a pH 7 in 100 mM Tris-HCl buffer solution in Example 10.

The table 8 and FIGS. 8-17 show the results. Approximately 50% of arsenous acid was methylated. The table 8 shows the concentration of the arsenic compound in the reaction solution.

TABLE 8

| No. | Time (hr) | As (V) | MMA (V) | MMA (III) | As (III) | DMA (V) | Total |
|---|---|---|---|---|---|---|---|
| 1 | 0.5 | 0.00 | 0.00 | 0.01 | 15.46 | 0.00 | 15.47 |
| 2 | 1 | 0.00 | 0.03 | 0.66 | 17.09 | 0.00 | 17.77 |
| 3 | 2 | 0.00 | 0.18 | 1.91 | 15.29 | 0.12 | 17.50 |
| 4 | 3 | 0.00 | 0.22 | 3.45 | 13.40 | 0.16 | 17.22 |
| 5 | 4 | 0.02 | 0.45 | 5.10 | 11.28 | 0.19 | 17.04 |
| 6 | 24 | 0.20 | 4.44 | 2.09 | 9.40 | 0.25 | 16.38 |
| 7 | 96 | 0.25 | 9.07 | 0.55 | 13.63 | 0.21 | 23.71 |
| 8 | 0.5 | 14.46 | 0.00 | 0.00 | 0.12 | 0.00 | 14.57 |
| 9 | 1 | 9.84 | 4.63 | 0.00 | 0.01 | 0.08 | 14.56 |
| 10 | 2 | 7.03 | 6.27 | 0.00 | 0.00 | 0.18 | 13.48 |
| 11 | 3 | 6.66 | 7.04 | 0.00 | 0.00 | 0.21 | 13.91 |
| 12 | 4 | 6.08 | 7.70 | 0.00 | 0.00 | 0.23 | 14.00 |
| 13 | 24 | 6.20 | 7.83 | 0.00 | 0.00 | 0.26 | 14.29 |
| 14 | 96 | 9.73 | 11.39 | 0.00 | 0.15 | 0.23 | 21.50 |

*No. 1-7: before $H_2O_2$ treatment.
**No. 8-14: after $H_2O_2$ treatment.

As it is clear from the table 8, it was revealed that it is possible to render them harmless by means of converting As(III) into As(V) with a high oxidation number, that is, increasing an oxidation number, by using $H_2O_2$ treatment.

Example 12

The experiment was carried out in the same manner as in Example 10, except that it was carried out under the condition that a pH of the reaction solution after preparation was a value shown in table 9.

The table 9 and FIGS. 18-29 show the results. Approximately 50% of arsenous acid in the case of a pH 6.7 was methylated. On the other hand, in the case of a pH 9, the methylation was not progressed. The table 9 shows the concentration of the arsenic compound in the reaction solution.

TABLE 9

| No. | pH | Time (hr) | H$_2$O$_2$ treatment | As (V) | MMA (V) | MMA (III) | As (III) | DMA (V) | UN6 | TMAO | Total |
|---|---|---|---|---|---|---|---|---|---|---|---|
| 1 | 4.3 | 1 | before | 1.0 | 1.0 | 0.0 | 22.8 | 0.0 | 0.0 | 0.0 | 24.9 |
| 2 | 4.3 | 2 | before | 1.0 | 1.6 | 0.8 | 21.3 | 0.9 | 1.0 | 0.0 | 26.6 |
| 3 | 4.3 | 4 | before | 1.0 | 2.2 | 1.1 | 20.1 | 1.0 | 1.0 | 0.0 | 26.4 |
| 4 | 4.3 | 24 | before | 1.1 | 3.3 | 1.5 | 13.6 | 1.0 | 0.9 | 0.0 | 21.4 |
| 5 | 4.3 | 1 | after | 17.8 | 0.0 | 0.0 | 0.0 | 0.0 | 0.0 | 0.0 | 17.8 |
| 6 | 4.3 | 2 | after | 17.7 | 1.1 | 0.0 | 0.0 | 0.9 | 0.0 | 0.0 | 19.7 |
| 7 | 4.3 | 4 | after | 12.7 | 5.3 | 0.0 | 0.0 | 1.0 | 0.0 | 0.0 | 18.9 |
| 8 | 4.3 | 24 | after | 8.9 | 6.3 | 0.0 | 0.0 | 1.0 | 0.0 | 0.0 | 16.2 |
| 9 | 6.7 | 1 | before | 1.6 | 1.8 | 0.6 | 21.4 | 0.0 | 0.0 | 0.0 | 25.3 |
| 10 | 6.7 | 2 | before | 1.5 | 4.0 | 0.6 | 18.5 | 0.9 | 0.0 | 0.0 | 25.4 |
| 11 | 6.7 | 4 | before | 1.3 | 6.3 | 0.6 | 15.2 | 1.0 | 0.0 | 0.0 | 24.5 |
| 12 | 6.7 | 24 | before | 1.3 | 5.1 | 1.4 | 11.1 | 1.0 | 0.0 | 0.0 | 19.9 |
| 13 | 6.7 | 1 | after | 18.1 | 0.0 | 0.0 | 0.0 | 0.0 | 0.0 | 0.0 | 18.1 |
| 14 | 6.7 | 2 | after | 12.9 | 5.3 | 0.0 | 0.0 | 0.9 | 0.0 | 0.0 | 19.1 |
| 15 | 6.7 | 4 | after | 10.1 | 8.1 | 0.0 | 0.0 | 1.0 | 0.0 | 0.0 | 19.3 |
| 16 | 6.7 | 24 | after | 8.2 | 6.8 | 0.0 | 0.0 | 1.0 | 0.0 | 0.0 | 16.0 |
| 17 | 9 | 1 | before | 8.2 | 0.0 | 0.0 | 12.9 | 0.0 | 1.0 | 0.0 | 22.1 |
| 18 | 9 | 2 | before | 10.0 | 0.0 | 0.0 | 10.8 | 0.0 | 1.0 | 0.0 | 21.9 |
| 19 | 9 | 4 | before | 10.9 | 0.0 | 0.0 | 9.6 | 0.0 | 1.1 | 0.0 | 21.6 |
| 20 | 9 | 24 | before | 13.0 | 0.0 | 0.0 | 1.8 | 0.0 | 0.0 | 0.0 | 14.9 |
| 21 | 9 | 1 | after | 18.3 | 0.0 | 0.0 | 0.0 | 0.0 | 0.0 | 0.0 | 18.3 |
| 22 | 9 | 2 | after | 18.0 | 0.0 | 0.0 | 0.0 | 0.0 | 0.0 | 0.0 | 18.0 |
| 23 | 9 | 4 | after | 18.1 | 0.0 | 0.0 | 0.0 | 0.0 | 0.0 | 0.0 | 18.1 |
| 24 | 9 | 24 | after | 14.4 | 0.0 | 0.0 | 0.0 | 0.0 | 0.0 | 0.0 | 14.4 |

Example 13

Next, the synthesis of [Cob(II)]ClO$_4$ from cyanocobalamin was attempted.

1. Oxidation-Reduction of the Cobalt Complex, and the Reaction of the Methylation (1) The Synthesis of [Cob(II)]ClO$_4$ from Cyanocobalamin <Reaction Scheme 1>

[Chemical 1]

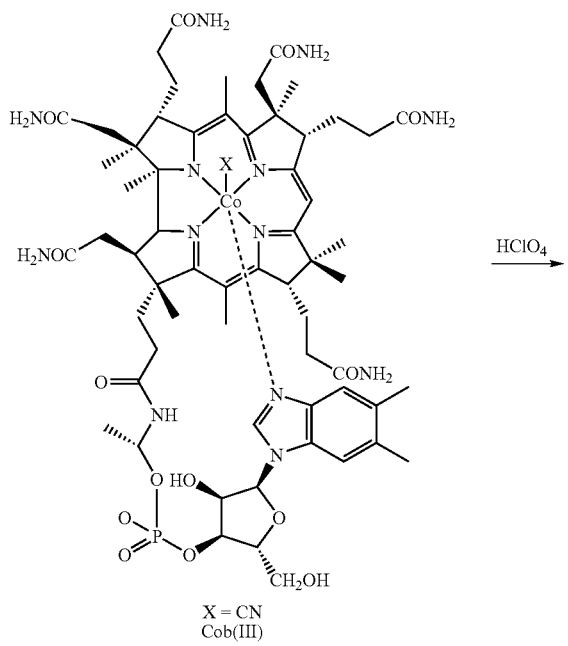

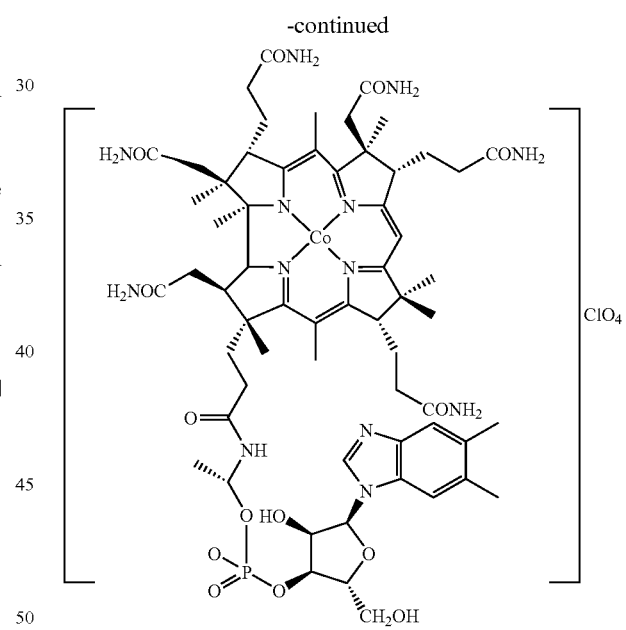

<Experiment Procedure>

50 mg of cyanocobalamin (which is Cob(III) shown in the above [chemical 1]) is dissolved in 100 mL of methanol, and then it is deaerated by a nitrogen bubbling. To this is added 400 mg of NaBH$_4$ (1.05 mol) to confirm a green color originated from Co(I). To this is added 3 mL of 60% HClO$_{4aq}$. To this is added 50 mL of water to extract with methylene chloride. After washed it with water, it is dried with anhydrous sodium sulfate so that it might be solidified under reduced pressure. This is re-precipitated with benzene/n-hexane to obtain a powder with an orange color.

(2) Reduction of [Cob(II)] to [Cob(I)]
<Reaction Scheme 2>

[Chemical 2]

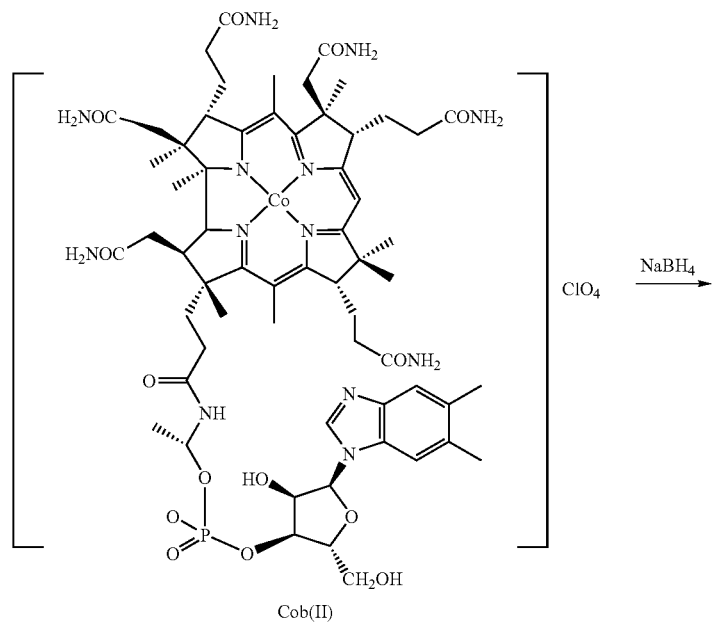

Cob(II)

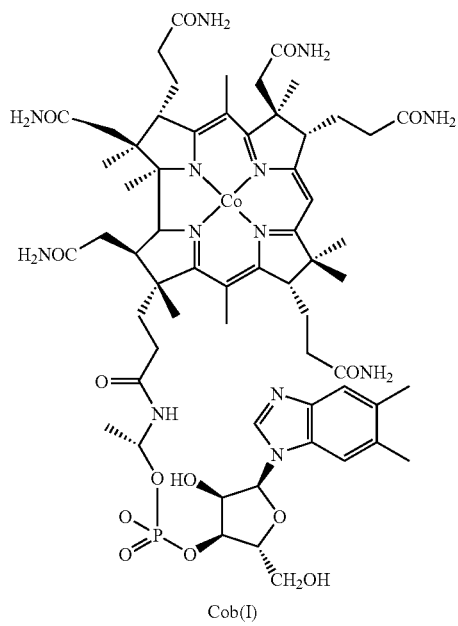

Cob(I)

<Experiment Procedure>

30 mg of [Cob(II)]ClO$_4$ is dissolved in 100 mL of methanol, and then it is deaerated by a nitrogen bubbling. To this is added 300 mg of NaBH$_4$ (0.788 mol) to confirm a green color originated from Co(I). It is recognized that in a viewpoint of the reaction of Cob(II) to Cob(I) shown in reaction scheme 2 [Chemical 2], the cobalt(III) complex existing in the composition for the alkylation of the present invention may convert to cobalt(II) complex, thereby cobalt(II) complex thus obtained is reduced by a photocatalyst or a chemical reducing agent as described in the following Example 14 to obtain a cobalt(I) complex. The cobalt (I) complex may be utilized as the substrate of the reaction of the dehalogenation. That is to say, it is possible to detoxify the organic halide compound by using the cobalt (I) complex thus obtained.

Example 14

Next, the synthesis of [MeCob(II)] by reacting [Cob(I)] with CH$_3$I (the reaction of the dehalogenation of the halide) was examined.

(3) The Synthesis of [MeCob(II)] by Reacting [Cob(I)] with CH₃I (the Reaction of the Dehalogenation of the Halide)
<Reaction Scheme 3>

[Chemical 3]

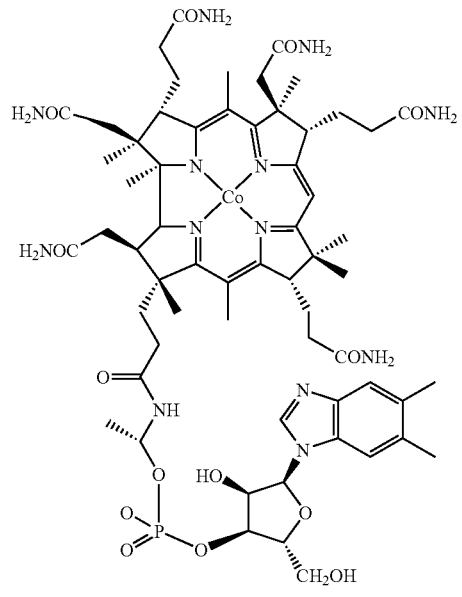

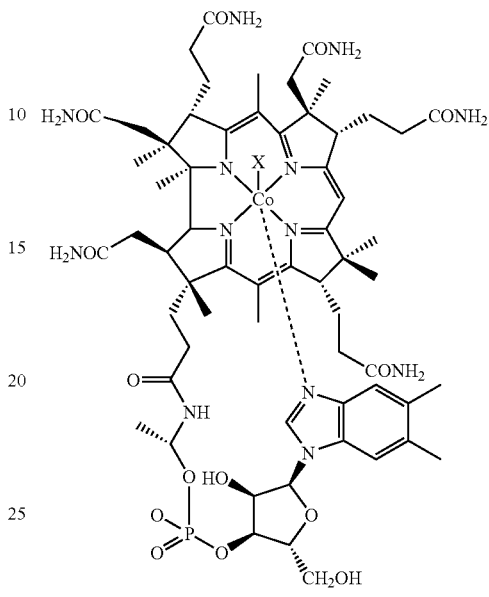

(4) The Synthesis of [MeCob(III)] from [MeCob(II)]
<Reaction Scheme 4>

[Chemical 4]

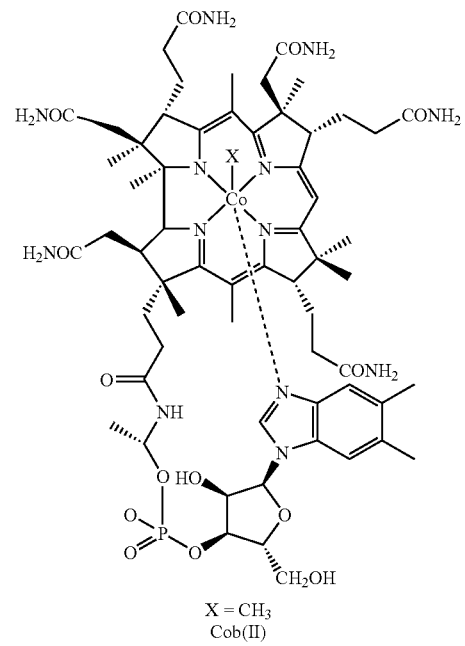

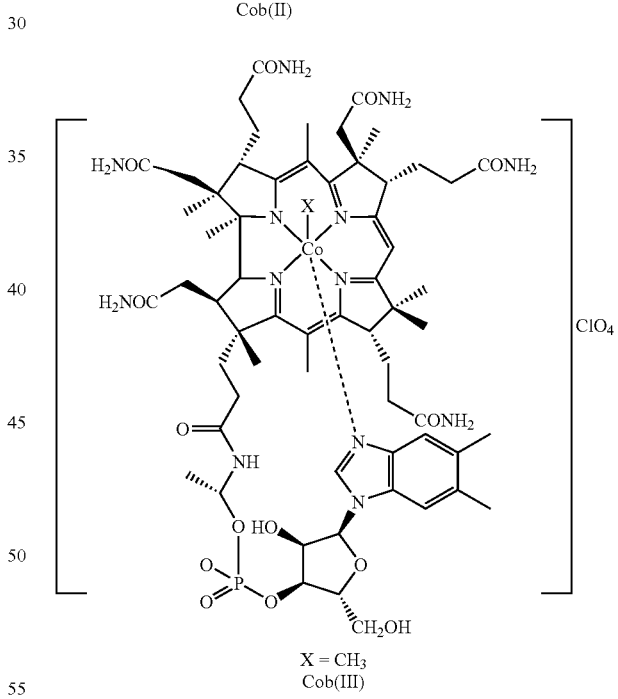

37 mg of CH₃I ($2.6 \times 10^{-4}$ mol) is added under the dark place, and stirred for 5 minutes. In this manner, the reaction of the dehalogenation is caused by the cobalt complex and the organic halide compound. That is, not only the organic halide compound which has been a harmful compound is detoxified by the dehalogenation, but the obtained cobalt (III) complex may become a preferable substrate to detoxify the harmful compound such as arsenic by the methylation.

<Experiment Procedure>
2 mL of 60% $HCl_{4aq}$ is added to the Cob(II). To this is added 50 mL of water to be extracted with methylene chloride. After washed them with water, they are dried with anhydrous sodium sulfate so as to be solidified under reduced pressure. They are re-precipitated with benzene/n-hexane to obtain a powder with an orange color, that is, methylcobalamin.

In this manner, it is possible to detoxify the organic halide compound or the harmful compound such as arsenic by utilizing the oxidation state of the cobalt complex existing in the composition for the alkylation of the present invention. In other words, it is also possible to detoxify the harmful compound by the methylation through the reaction of the cobalt (III) complex with the harmful compound (which contains arsenic etc.) with the use of the cobalt (III) complex obtained by the dehalogenation reaction of the organic halide compound with cobalt (I) complex.

On the other hand, if the generated cobalt (II) complex is reduced through any reaction, a cobalt (I) complex may be obtained, thereby the use of the cobalt complex thus obtained making it possible to detoxify the organic halide compound again.

Example 15

Next, under given conditions, with the use of GSH and methylcobalamin, the most efficient case capable of converting to TMAO was examined.

At first, into a 0.2 mL of Eppendorf tube GSH (60 mg, 0.195 mmol), 10 mg of methylcobalamin (MC) (7.44 μmol), Tris-HCl buffer solution (pH 8, 50 μL) were added. To this was added 2 mL of arsenic standard solution (for an atomic absorption: 100 ppm as arsenic), thereby set on an aluminium block heater heated at 125° C. to react them for predetermined time. The product of a reaction was diluted with 10% of hydrogen peroxide solution by 10-30 folds so that the product might be analyzed by the HPLC-ICP-MS. The result of this is shown in tables 10 and 11.

The tables 10 and 11 show a result of the HPLC-ICP-MS analysis in the case that the concentration of GSH, the concentration of arsenic and temperature etc., are changed. The table 10 is expressed in the concentration, and the table 11 is expressed in the percentage.

As a result, under the condition of the present Example, it is revealed that MC115 of the table 10 and 11 is the best data which makes it possible to convert the harmful compound into approximately 100% of TMAO by using GSH.

Example 16

Next, the effect was examined with the use of cysteine (Cys) instead of GSH. At first, into a 0.2 mL of Eppendorf tube, cysteine (20 mg, 0.165 mmol) as the reducing agent instead of GSH, methylcobalamin (MC) (20 mg, 14.9 μmol.), phosphate buffer solution (pH 6, 100 μL) were added. To this was added 4 μL of arsenic standard solution (for an atomic absorption: 100 ppm as arsenic), thereby set on an aluminium block heater heated at 110° C. to react them for predetermined time. The product of a reaction was diluted with 10% of hydrogen peroxide solution by 10-30 folds so that the product might be analyzed by the HPLC-ICP-MS. The result of this is shown in table 12.

TABLE 10

| concentration Sample | GSH (mg) | MC (mg) | pH | reaction temp. (° C.) | reaction time (h) | As (III) | As (V) | MMA | DMA | TMAO | TeMA | (ppm) Total |
|---|---|---|---|---|---|---|---|---|---|---|---|---|
| MC111-1p | 10 | 5 | 8 | 125 | 2 | 0.00 | 0.00 | 0.00 | 0.00 | 0.54 | 0.05 | 0.59 |
| MC112-1p | 20 | 5 | 8 | 125 | 2 | 0.00 | 0.00 | 0.00 | 0.02 | 0.50 | 0.00 | 0.52 |
| MC113-1p | 30 | 5 | 8 | 125 | 2 | 0.00 | 0.00 | 0.00 | 0.02 | 0.43 | 0.00 | 0.46 |
| MC114-1p | 20 | 10 | 8 | 125 | 2 | 0.00 | 0.00 | 0.00 | 0.00 | 1.79 | 0.04 | 1.83 |
| MC115-1p | 40 | 10 | 8 | 125 | 2 | 0.00 | 0.00 | 0.00 | 0.00 | 1.56 | 0.01 | 1.57 |
| MC116-1p | 60 | 10 | 8 | 125 | 2 | 0.00 | 0.00 | 0.00 | 0.03 | 1.73 | 0.00 | 1.77 |
| MC117-1p | 20 | 10 | 8 | 100 | 2 | 0.00 | 0.03 | 0.09 | 0.02 | 2.83 | 0.00 | 2.97 |
| MC118-1p | 40 | 10 | 8 | 100 | 2 | 0.00 | 0.00 | 0.00 | 0.00 | 0.00 | 0.00 | 0.00 |
| MC119-1p | 60 | 10 | 8 | 100 | 2 | 0.00 | 0.00 | 0.29 | 0.38 | 5.14 | 0.02 | 5.83 |
| MC120-1p | 0 | 10 | 8 | 125 | 2 | 0.06 | 1.27 | 0.36 | 0.04 | 0.13 | 1.59 | 3.46 |
| MC117-2p | 10 | 10 | 8 | 100 | over night | 0.00 | 0.03 | 0.01 | 0.00 | 3.35 | 0.00 | 3.39 |
| MC118-2p | 20 | 10 | 8 | 100 | over night | 0.00 | 0.00 | 0.00 | 0.00 | 0.00 | 0.00 | 0.00 |
| MC119-2p | 30 | 10 | 8 | 100 | over night | 0.00 | 0.00 | 0.02 | 0.07 | 2.68 | 0.00 | 2.78 |

TABLE 11

| Sample | GSH (mg) | MC (mg) | pH | reaction temp. (° C.) | reaction time (h) | As (III) | As (V) | MMA | DMA | TMAO | TeMA | Total |
|---|---|---|---|---|---|---|---|---|---|---|---|---|
| MC111-1p | 10 | 5 | 8 | 125 | 2 | 0.0 | 0.0 | 0.0 | 0.0 | 91.1 | 8.9 | 100 |
| MC112-1p | 20 | 5 | 8 | 125 | 2 | 0.0 | 0.0 | 0.0 | 3.6 | 96.4 | 0.0 | 100 |
| MC113-1p | 30 | 5 | 8 | 125 | 2 | 0.0 | 0.0 | 0.0 | 5.1 | 94.9 | 0.0 | 100 |
| MC114-1p | 20 | 10 | 8 | 125 | 2 | 0.0 | 0.0 | 0.0 | 0.0 | 97.8 | 2.2 | 100 |
| MC115-1p | 40 | 10 | 8 | 125 | 2 | 0.0 | 0.0 | 0.0 | 0.1 | 99.2 | 0.7 | 100 |
| MC116-1p | 60 | 10 | 8 | 125 | 2 | 0.0 | 0.0 | 0.0 | 1.9 | 98.1 | 0.0 | 100 |
| MC117-1p | 20 | 10 | 8 | 100 | 2 | 0.0 | 1.0 | 3.0 | 0.6 | 95.4 | 0.0 | 100 |
| MC119-1p | 60 | 10 | 8 | 100 | 2 | 0.0 | 0.0 | 5.0 | 6.6 | 88.2 | 0.3 | 100 |
| MC120-1p | 0 | 10 | 8 | 125 | 2 | 1.7 | 36.9 | 10.3 | 1.2 | 3.9 | 46.1 | 100 |
| MC117-2p | 10 | 10 | 8 | 100 | over night | 0.0 | 0.8 | 0.3 | 0.0 | 98.9 | 0.0 | 100 |
| MC119-2p | 30 | 10 | 8 | 100 | over night | 0.0 | 0.0 | 0.9 | 2.6 | 96.5 | 0.0 | 100 |

TABLE 12

| Sample | Cys (mg) | MC (mg) | pH | Buffer (mL) | reaction temperature (°C.) | reaction time (h) | As (V) | MMA | DMA | TMAO | TeMA | Total | TMAO ratio (g) |
|---|---|---|---|---|---|---|---|---|---|---|---|---|---|
| MC151-1p | 30 | 20 | 8 | 0.1 | 120 | 1.5 | 4.5 | 9.3 | 6.9 | 33.9 | 0.0 | 54.6 | 62.1 |
| MC152-1p | 20 | 20 | 8 | 0.1 | 120 | 1.5 | 0.3 | 2.7 | 1.2 | 3.9 | 0.9 | 9.0 | 43.3 |
| MC153-1p | 10 | 20 | 8 | 0.1 | 120 | 1.5 | 13.2 | 5.1 | 5.4 | 25.2 | 5.1 | 54.0 | 46.7 |
| MC154-1p | 30 | 20 | 8 | 0.1 | 110 | 1.5 | 5.4 | 10.5 | 7.8 | 55.5 | 8.1 | 87.3 | 63.6 |
| MC155-1p | 20 | 20 | 8 | 0.1 | 110 | 1.5 | 2.1 | 4.5 | 4.5 | 20.1 | 4.5 | 35.7 | 56.3 |
| MC156-1p | 10 | 20 | 8 | 0.1 | 110 | 1.5 | 2.4 | 0.0 | 0.0 | 0.0 | 0.0 | 2.4 | 0.0 |
| MC157-1p | 20 | 20 | 6 | 0.1 | 110 | 1.5 | 2.7 | 3.3 | 0.0 | 26.1 | 3.6 | 35.7 | 73.1 |
| MC158-1p | 20 | 20 | 7 | 0.1 | 110 | 1.5 | 1.5 | 5.7 | 6.0 | 15.9 | 3.3 | 32.4 | 49.1 |
| MC159-1p | 20 | 20 | 8 | 0.1 | 110 | 1.5 | 3.0 | 12.9 | 12.3 | 27.6 | 3.3 | 59.1 | 46.7 |
| MC160-1p | 0 | 20 | 8 | 0.1 | 110 | 1.5 | 115.5 | 0.0 | 0.0 | 0.0 | 0.0 | 115.5 | 0.0 |
| MC151-2p | 30 | 20 | 8 | 0.1 | 120 | 14 | 16.8 | 29.4 | 26.4 | 132.6 | 5.7 | 210.9 | 62.9 |
| MC152-2p | 20 | 20 | 8 | 0.1 | 120 | 14 | 15.3 | 12.9 | 26.7 | 180.3 | 17.4 | 252.6 | 71.4 |
| MC153-2p | 10 | 20 | 8 | 0.1 | 120 | 14 | 13.2 | 8.7 | 34.5 | 173.1 | 21.6 | 251.1 | 68.9 |
| MC154-2p | 30 | 20 | 8 | 0.1 | 110 | 14 | 6.6 | 16.8 | 15.0 | 130.5 | 8.4 | 177.3 | 73.6 |
| MC155-2p | 20 | 20 | 8 | 0.1 | 110 | 14 | 10.2 | 13.2 | 18.9 | 192.3 | 22.2 | 256.8 | 74.9 |
| MC156-2p | 10 | 20 | 8 | 0.1 | 110 | 14 | 17.1 | 0.0 | 14.4 | 186.9 | 21.0 | 239.4 | 78.1 |
| MC157-2p | 20 | 20 | 6 | 0.1 | 110 | 14 | 8.4 | 10.8 | 12.6 | 261.6 | 19.2 | 312.6 | 83.7 |
| MC158-2p | 20 | 20 | 7 | 0.1 | 110 | 14 | 7.8 | 9.9 | 18.3 | 192.9 | 15.3 | 244.2 | 79.0 |
| MC159-2p | 20 | 20 | 8 | 0.1 | 110 | 14 | 13.2 | 19.8 | 62.1 | 223.8 | 14.1 | 333.0 | 67.2 |
| MC160-2p | 0 | 20 | 8 | 0.1 | 110 | 14 | 431.4 | 0.0 | 0.0 | 5.1 | 23.1 | 459.6 | 1.1 |
| MC151-3p | 30 | 20 | 8 | 0.1 | 120 | 26 | 14.4 | 0.0 | 78.0 | 129.6 | 0.0 | 222.0 | 58.4 |
| MC152-3p | 20 | 20 | 8 | 0.1 | 120 | 26 | 90.3 | 45.3 | 371.7 | 1883.7 | 120.9 | 2511.9 | 75.0 |
| MC153-3p | 10 | 20 | 8 | 0.1 | 120 | 26 | 171.3 | 96.0 | 391.2 | 1985.7 | 195.3 | 2839.5 | 69.9 |
| MC154-3p | 30 | 20 | 8 | 0.1 | 110 | 26 | 0.0 | 0.0 | 72.3 | 295.2 | 0.0 | 367.5 | 80.3 |
| MC155-3p | 20 | 20 | 8 | 0.1 | 110 | 26 | 72.9 | 0.0 | 155.1 | 1089.0 | 1.8 | 1318.8 | 82.6 |
| MC156-3p | 10 | 20 | 8 | 0.1 | 110 | 26 | 52.2 | 27.6 | 84.9 | 1118.1 | 65.1 | 1347.9 | 83.0 |
| MC157-3p | 20 | 20 | 6 | 0.1 | 110 | 26 | 0.0 | 21.0 | 50.7 | 497.7 | 0.0 | 569.4 | 87.4 |
| MC158-3p | 20 | 20 | 7 | 0.1 | 110 | 26 | 3.9 | 13.5 | 169.8 | 1140.0 | 85.8 | 1413.0 | 80.7 |
| MC159-3p | 20 | 20 | 8 | 0.1 | 110 | 26 | 13.8 | 35.1 | 366.6 | 1066.2 | 14.4 | 1496.1 | 71.3 |
| MC160-3p | 0 | 20 | 8 | 0.1 | 110 | 26 | 1587.0 | 0.0 | 0.0 | 0.0 | 4.5 | 1591.5 | 0.0 |

The table 12 shows a result of the HPLC-ICP-MS analysis in the case that the concentration of cysteine, the concentration of arsenic and temperature etc., are changed. It is revealed that an excellent result is produced in the same as GSH even if cysteine instead of GSH is used. Especially, if the ratio of TMAO is noted, MC157-3p of the table 12 has an excellent result.

Example 17

Next, the effect was also examined with the use of homocysteine instead of GSH. At first, into a 0.2 mL of Eppendorf tube, homocysteine (HCys) (5 mg, 16.3 μmol.) as the reducing agent instead of GSH, methylcobalamin (MC) (20 mg, 14.9 μmol.), phosphate buffer solution (pH 6, 100 μL) were added. To this was added 4 μL of an arsenic standard solution (for an atomic absorption: 100 ppm as arsenic), thereby set on an aluminium block heater heated at 120° C. to react them for predetermined time. The product of a reaction was diluted with 10% of hydrogen peroxide solution by 10-30 folds so that the product might be analyzed by the HPLC-ICP-MS. The result of this is shown in table 13.

TABLE 13

| Sample | HCys (mg) | MC (mg) | pH | Buffer (mL) | reaction temp. (°C.) | reaction time (h) | As (V) | MMA | DMA | TMAO | TeMA | Total | TMAO ratio (%) |
|---|---|---|---|---|---|---|---|---|---|---|---|---|---|
| MC161-1p | 10 | 20 | 8 | 0.1 | 120 | 1.5 | 27.3 | 20.1 | 6.6 | 78.9 | 11.1 | 132.9 | 59 |
| MC162-1p | 7.5 | 20 | 8 | 0.1 | 120 | 1.5 | 13.2 | 8.4 | 4.2 | 73.8 | 16.5 | 99.6 | 74 |
| MC163-1p | 5 | 20 | 8 | 0.1 | 120 | 1.5 | 19.2 | 8.7 | 7.5 | 142.8 | 61.8 | 178.2 | 80 |
| MC164-1p | 10 | 20 | 8 | 0.1 | 110 | 1.5 | 17.7 | 13.8 | 4.5 | 78.3 | 8.1 | 114.3 | 69 |
| MC165-1p | 7.5 | 20 | 8 | 0.1 | 110 | 1.5 | 28.2 | 13.8 | 8.4 | 86.7 | 12.6 | 137.1 | 63 |
| MC166-1p | 5 | 20 | 8 | 0.1 | 110 | 1.5 | 23.7 | 9.9 | 7.2 | 112.8 | 27.9 | 153.6 | 73 |
| MC167-1p | 7.5 | 20 | 6 | 0.1 | 110 | 1.5 | 46.5 | 21.3 | 8.1 | 110.4 | 20.1 | 186.3 | 59 |
| MC168-1p | 7.5 | 20 | 7 | 0.1 | 110 | 1.5 | 16.5 | 9.0 | 6.3 | 80.4 | 20.7 | 112.2 | 72 |
| MC169-1p | 7.5 | 20 | 8 | 0.1 | 110 | 1.5 | 22.2 | 9.0 | 10.8 | 68.4 | 16.5 | 110.4 | 62 |
| MC170-1p | 0 | 20 | 8 | 0.1 | 110 | 1.5 | 367.2 | 0.0 | 0.0 | 0.0 | 0.0 | 367.2 | 0 |
| MC161-2p | 10 | 20 | 8 | 0.1 | 120 | 14 | 9.6 | 7.2 | 22.5 | 203.1 | 18.3 | 242.4 | 84 |
| MC162-2p | 7.5 | 20 | 8 | 0.1 | 120 | 14 | 14.7 | 16.2 | 18.6 | 298.5 | 51.3 | 348.0 | 86 |
| MC163-2p | 5 | 20 | 8 | 0.1 | 120 | 14 | 10.8 | 9.0 | 13.2 | 227.7 | 99.0 | 260.7 | 87 |
| MC164-2p | 10 | 20 | 8 | 0.1 | 110 | 14 | 12.3 | 7.5 | 16.8 | 191.1 | 17.4 | 227.7 | 84 |
| MC165-2p | 7.5 | 20 | 8 | 0.1 | 110 | 14 | 36.6 | 24.6 | 23.7 | 264.3 | 23.1 | 349.2 | 76 |
| MC166-2p | 5 | 20 | 8 | 0.1 | 110 | 14 | 18.3 | 18.6 | 19.8 | 328.5 | 60.3 | 385.2 | 85 |
| MC167-2p | 7.5 | 20 | 6 | 0.1 | 110 | 14 | 21.3 | 10.5 | 13.8 | 222.6 | 23.4 | 268.2 | 83 |

TABLE 13-continued

| | reaction conditions | | | | | | content of the arsenic compound (ng As/mL) | | | | | | TMAO |
|---|---|---|---|---|---|---|---|---|---|---|---|---|---|
| Sample | HCys (mg) | MC (mg) | pH | Buffer (mL) | reaction temp. (° C.) | reaction time (h) | As (V) | MMA | DMA | TMAO | TeMA | Total | ratio (%) |
| MC168-2p | 7.5 | 20 | 7 | 0.1 | 110 | 14 | 15.3 | 11.7 | 20.1 | 248.4 | 23.7 | 295.5 | 84 |
| MC169-2p | 7.5 | 20 | 8 | 0.1 | 110 | 14 | 12.6 | 8.7 | 18.3 | 141.0 | 12.6 | 180.6 | 78 |
| MC170-2p | 0 | 20 | 8 | 0.1 | 110 | 14 | 214.2 | 0.0 | 0.0 | 0.0 | 6.6 | 214.2 | 0 |
| MC161-3p | 10 | 20 | 8 | 0.1 | 120 | 26 | 146.1 | 124.8 | 138.0 | 1245.3 | 84.3 | 1654.2 | 75 |
| MC162-3p | 7.5 | 20 | 8 | 0.1 | 120 | 26 | 183.9 | 123.0 | 107.4 | 1655.1 | 205.3 | 2059.4 | 80 |
| MC163-3p | 5 | 20 | 8 | 0.1 | 120 | 26 | 82.2 | 51.6 | 50.1 | 940.2 | 343.2 | 1124.1 | 84 |
| MC164-3p | 10 | 20 | 8 | 0.1 | 110 | 26 | 385.8 | 201.6 | 104.1 | 1437.3 | 36.0 | 2128.8 | 68 |
| MC165-3p | 7.5 | 20 | 8 | 0.1 | 110 | 26 | 264.0 | 121.2 | 88.8 | 1056.6 | 14.4 | 1530.6 | 69 |
| MC166-3p | 5 | 20 | 8 | 0.1 | 110 | 26 | 69.0 | 79.2 | 50.7 | 1035.9 | 135.9 | 1234.8 | 84 |
| MC167-3p | 7.5 | 20 | 6 | 0.1 | 110 | 26 | 126.6 | 90.0 | 58.5 | 1204.5 | 65.4 | 1479.6 | 81 |
| MC168-3p | 7.5 | 20 | 7 | 0.1 | 110 | 26 | 170.4 | 87.0 | 94.2 | 1163.4 | 51.0 | 1515.0 | 77 |
| MC169-3p | 7.5 | 20 | 8 | 0.1 | 110 | 26 | 104.1 | 84.3 | 126.0 | 1110.9 | 42.3 | 1425.3 | 78 |
| MC170-3p | 0 | 20 | 8 | 0.1 | 110 | 26 | 2700.3 | 0.0 | 0.0 | 0.0 | 0.0 | 2700.3 | 0 |

The table 13 shows a result of the HPLC-ICP-MS analysis in the case that the concentration of homocysteine, the concentration of arsenic and temperature etc., are changed. It is revealed that an excellent result is obtained in the same as GSH even if homocysteine instead of GSH is used. Especially, if the ratio of TMAO is noted, MC163-2p of the table 13 has an excellent result.

Example 18

Next, the effect was also examined with the use of thioglycol in addition to GSH. That is, the effect in the case of the addition of a high boiling point solvent was examined. Specifically, thioglycol (TG, $HSCH_2CH_2OH$, boiling point: 157° C.) with the SH group and dimethyl sulfoxide (DMSO, $(CH_3)_2SO$, boiling point: 189° C.) with no SH group were used.

At first, into a 0.2 mL of Eppendorf tube, GSH (4 mg, 13 μmol.) as the reducing agent, methylcobalamin (MC) (1 mg, 0.74 μmol.), TG (5 μL), Tris-HCl buffer solution (pH 8, 5 μL) were added. To this was added 2 μL of an arsenic standard solution (10 ppm as arsenic), thereby set on an aluminium block heater heated at 120° C. to react them for predetermined time. The product of a reaction was diluted with 10% of hydrogen peroxide solution by 10-30 times so that the product might be analyzed by the HPLC-ICP-MS (the explanation of MC179 etc., of the tables 14 and 15).

Moreover, concerning MC180 of tables 14 and 15, into a 0.2 mL of Eppendorf tube, GSH (4 mg, 13 μmol.) as the reducing agent, methylcobalamin (MC) (1 mg, 0.74 μmol.), DMSO (5 mL), Tris-HCl buffer solution (pH 8, 5 μL) were added. To this was added 2 mL of the arsenic standard solution (10 ppm as arsenic), thereby set on an aluminium block heater heated at 120° C. to react them for predetermined time. The product of a reaction was diluted with 10% of hydrogen peroxide solution by 10-30 folds so that the product might be analyzed by the HPLC-ICP-MS. The results of these are shown in tables 14 and 15.

TABLE 14

| | conditions of the recation | | | | | | | content of the arsenic compound (mg As/L) | | | | | | |
|---|---|---|---|---|---|---|---|---|---|---|---|---|---|---|
| Sample | GSH (mg) | MC (mg) | Buffer (μL) | TG (μL) | DMSO (μL) | reaction time (h) | reaction temp. (° C.) | UN | As (III) | As (V) | MMA | DMA | TMAO | TeMA | Total |
| MC179 | 4 | 1 | 5 | 5 | 0 | 2 | 120 | 0.084 | 0.010 | 0.000 | 0.982 | 0.452 | 0.171 | 0.027 | 1.725 |
| MC180 | 4 | 1 | 5 | 0 | 5 | 2 | 120 | 0.572 | 0.000 | 0.000 | 0.969 | 0.117 | 0.083 | 0.000 | 1.740 |

TABLE 15

| | onditions of the reaction | | | | | | | ratio of the arsenic compound (%) | | | | | | |
|---|---|---|---|---|---|---|---|---|---|---|---|---|---|---|
| Sample | GSH (mg) | MC (mg) | Buffer (μL) | TG (μL) | DMSO (μL) | reaction time (h) | reaction temp. (° C.) | UN | As (III) | As (V) | MMA | DMA | TMAO | TeMA | Total |
| MC179 | 4 | 1 | 5 | 5 | 0 | 2 | 120 | 4.9 | 0.6 | 0.0 | 56.9 | 26.2 | 9.9 | 1.5 | 100.0 |
| MC180 | 4 | 1 | 5 | 0 | 5 | 2 | 120 | 32.9 | 0.0 | 0.0 | 55.7 | 6.7 | 4.8 | 0.0 | 100.0 |

The tables 14 and 15 show a result of the HPLC-ICP-MS analysis in the case of the use of TG, DMSO in addition to GSH (in tables 14 and 15, GSH: glutathione (reduced form), MC: methylcobalamin, TG: thioglycol, DMSO: dimethyl sulfoxide.). The table 14 is those expressed in the concentration, and the table 15 is those expressed in the percentage. It is revealed that an excellent result can be obtained in the same as the case of the use of GSH by itself, even if in the case that TG and DMSO are used.

Example 19

Next, the effect was further examined with the use of Cysteine (Cys) as the reducing agent in the same manner as the above example. The table 16 shows a methylation reaction (Acid condition) (Reacting substance) of arsenic trioxide [iAs (III)] by MC.

TABLE 16

|  |  | reactant | | | solvent | ratio of stoichiometry | |
| --- | --- | --- | --- | --- | --- | --- | --- |
| exp. No. | exp. No. | Cys (μmol) | MC (μmol) | iAs (III) (nmol) | 1N HCl (μL) | reductant [Cys]/[As] | methylating agent [MC]/[As] |
| MC394 | 1 | 165.1 | 0.7 | 2.7 | 50 | 61902 | 279 |
| MC395 | 2 | 165.1 | 3.7 | 2.7 | 50 | 61902 | 1395 |
| MC396 | 3 | 165.1 | 7.4 | 2.7 | 50 | 61902 | 2789 |
| MC397 | 4 | 165.1 | 14.9 | 2.7 | 50 | 61902 | 5579 |
| MC398 | 5 | 165.1 | 22.3 | 2.7 | 50 | 61902 | 8368 |
| MC399 | 6 | 165.1 | 29.8 | 2.7 | 50 | 61902 | 11158 |
| MC393 | 7 | 165.1 | 37.2 | 2.7 | 50 | 61902 | 13947 |

The table 17 shows a methylation reaction (Acid condition) (Reaction condition and product of a reaction) of arsenic trioxide [iAs (III)] by MC. In the table, GSH: reduced glutathione, MC: methylcobalamin, As: starting material (It is trivalent arsenic: iAs (III).), MMA: monomethylated arsenic acid, DMA: dimethylarsineoxide, TMAO: trimethylarsineoxide and TeMA: tetramethyl arsenic, respectively, a value was calculated as a conversion ratio=100% ([iAs (V)]+[MMA]+[DMA]+[TMAO]+[TeMA])/[iAs (III)]).

TABLE 17

| | reaction condition | | relative ratio | | | | | | conversion |
| --- | --- | --- | --- | --- | --- | --- | --- | --- | --- |
| exp. No. | Temp. (° C.) | Time (hr) | iAs5 (%) | MMA (%) | DMA (%) | TMAO (%) | TeMA (%) | total (%) | ratio (%) |
| 1 | 100 | 2 | 8 | 43 | 10 | 40 | 0 | 100 | 71 |
| 2 | 100 | 2 | 0 | 0 | 0 | 83 | 17 | 100 | 77 |
| 3 | 100 | 2 | 0 | 0 | 0 | 57 | 43 | 100 | 84 |
| 4 | 100 | 2 | 0 | 0 | 0 | 31 | 69 | 100 | 83 |
| 5 | 100 | 2 | 0 | 0 | 0 | 16 | 84 | 100 | 97 |
| 6 | 100 | 2 | 0 | 0 | 0 | 11 | 89 | 100 | 100 |
| 7 | 100 | 2 | 0 | 0 | 0 | 6 | 94 | 100 | 98 |

The table 18 shows a methylation reaction (Neutral condition) (Reacting substance) of arsenic trioxide [iAs (III)] by MC.

TABLE 18

| | reactant | | | solvent | ratio of stoichiometry | |
| --- | --- | --- | --- | --- | --- | --- |
| exp. No. | Cys (μmol) | MC (μmol) | iAs (III) (nmol) | buffer (pH 8) (μL) | reductant [Cys]/[As] | methylating agent [MC]/[As] |
| 1 | 165.1 | 14.9 | 2.7 | 50 | 61902 | 5579 |
| 2 | 165.1 | 22.3 | 2.7 | 50 | 61902 | 8368 |
| 3 | 165.1 | 29.8 | 2.7 | 50 | 61902 | 11158 |
| 4 | 165.1 | 37.2 | 2.7 | 50 | 61902 | 13947 |
| 5 | 165.1 | 44.6 | 2.7 | 50 | 61902 | 16736 |
| 6 | 165.1 | 52.1 | 2.7 | 50 | 61902 | 19526 |
| 7 | 165.1 | 31.2 | 2.7 | 50 | 61902 | 13947 |

The table 19 shows a methylation reaction (Neutral condition) (Reaction condition and product of a reaction) of arsenic trioxide [iAs (III)] by MC.

TABLE 19

| exp. No. | reaction condition | | relative ratio | | | | | | conversion |
|---|---|---|---|---|---|---|---|---|---|
| | Temp. (° C.) | Time (hr) | iAs (V) (%) | MMA (%) | DMA (%) | TMAO (%) | TeMA (%) | total (%) | ratio (%) |
| 1 | 100 | 2 | 7 | 3 | 3 | 74 | 13 | 100 | 55 |
| 2 | 100 | 2 | 7 | 0 | 3 | 68 | 22 | 100 | 42 |
| 3 | 100 | 2 | 0 | 0 | 0 | 80 | 20 | 100 | 44 |
| 4 | 100 | 2 | 0 | 0 | 0 | 79 | 21 | 100 | 41 |
| 5 | 100 | 2 | 0 | 0 | 0 | 67 | 33 | 100 | 42 |
| 6 | 100 | 2 | 0 | 0 | 0 | 66 | 34 | 100 | 31 |
| 7 | 100 | 2 | 10 | 0 | 0 | 79 | 11 | 100 | 81 |

The table 20 shows a methylation reaction (Alkali condition) (Reacting substance) of arsenic trioxide [iAs (III)] by MC.

TABLE 20

| exp. No. | reactant | | | solvent | ratio of stoichiometry | |
|---|---|---|---|---|---|---|
| | Cys (μmol) | MC (μmol) | iAs (III) (nmol) | 1 mol/L NaOH (μmol) | reductant [Cys]/[As] | methylating agent [MC]/[As] |
| 1 | 165.1 | 0.1 | 2.7 | 50 | 61902 | 28 |
| 2 | 165.1 | 0.4 | 2.7 | 50 | 61902 | 139 |
| 3 | 165.1 | 0.7 | 2.7 | 50 | 61902 | 279 |
| 4 | 165.1 | 3.7 | 2.7 | 50 | 61902 | 1395 |
| 5 | 165.1 | 7.4 | 2.7 | 50 | 61902 | 2789 |
| 6 | 165.1 | 14.9 | 2.7 | 50 | 61902 | 5579 |
| 7 | 165.1 | 14.9 | 2.7 | 50 | 61902 | 5579 |
| 8 | 165.1 | 22.3 | 2.7 | 50 | 61902 | 8368 |
| 9 | 165.1 | 29.8 | 2.7 | 50 | 61902 | 11158 |
| 10 | 165.1 | 37.2 | 2.7 | 50 | 61902 | 13947 |
| 11 | 165.1 | 44.6 | 2.7 | 50 | 61902 | 16736 |
| 12 | 165.1 | 52.1 | 2.7 | 50 | 61902 | 19526 |
| 13 | 165.1 | 37.2 | 2.7 | 50 | 61902 | 13947 |
| 14 | 165.1 | 37.2 | 2.7 | 50 | 61902 | 13947 |

The table 21 shows a methylation reaction (Alkali condition) (Reaction condition and product of a reaction) of arsenic trioxide [iAs (III)] by MC.

TABLE 21

| exp. No. | reaction condition | | relative ratio | | | | | | conversion |
|---|---|---|---|---|---|---|---|---|---|
| | Temp. (° C.) | Time (hr) | iAs (V) (%) | MMA (%) | DMA (%) | TMAO (%) | TeMA (%) | total (%) | ratio (%) |
| 1 | 100 | 2 | 100 | 0 | 0 | 0 | 0 | 100 | 112 |
| 2 | 100 | 2 | 96 | 4 | 0 | 0 | 0 | 100 | 118 |
| 3 | 100 | 2 | 93 | 7 | 0 | 0 | 0 | 100 | 114 |
| 4 | 100 | 2 | 37 | 24 | 7 | 30 | 2 | 100 | 115 |
| 5 | 100 | 2 | 15 | 23 | 14 | 45 | 3 | 100 | 107 |
| 6 | 100 | 2 | 9 | 5 | 9 | 73 | 4 | 100 | 109 |
| 7 | 100 | 2 | 16 | 7 | 7 | 67 | 3 | 100 | 102 |
| 8 | 100 | 2 | 10 | 3 | 18 | 67 | 2 | 100 | 99 |
| 9 | 100 | 2 | 1 | 0 | 7 | 89 | 4 | 100 | 84 |
| 10 | 100 | 2 | 3 | 0 | 4 | 90 | 3 | 100 | 95 |
| 11 | 100 | 2 | 2 | 0 | 6 | 88 | 4 | 100 | 93 |
| 12 | 100 | 2 | 3 | 0 | 4 | 88 | 5 | 100 | 86 |
| 13 | 100 | 2 | 6 | 0 | 6 | 85 | 3 | 100 | 91 |
| 14 | 100 | 2 | 7 | 0 | 4 | 88 | 4 | 100 | 95 |

Example 20

Figure 32:
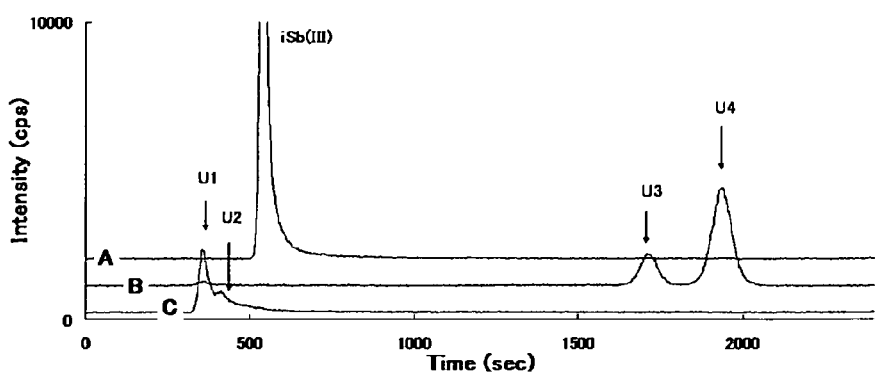
FIG. 32 gives a HPLC-ICP-MS chromatogram (measurement element Sb, m/z 121).

Next, a detoxification of antimony was examined in the same manner as the above mentioned example. FIG. 32 gives a HPLC-ICP-MS chromatogram (Measurement element: Sb, m/z 121). In the figure, A: standard sample [iSb (III)], B: sample after the reaction (MC+GSH), C: sample after the reaction (Only MC). The table 22 shows a methylation reaction (Reacting substance and reaction condition) of an inorganic antimony.

TABLE 22

| | reactant | | | | reaction condition | |
|---|---|---|---|---|---|---|
| No. | GSH (µmol) | MC (µmol) | buffer (pH 8) (µL) | iSb (III) (nmol) | Temp. (° C.) | Time (hr) |
| 1 | 65.1 | 7.4 | 50 | 2.7 | 100 | 2 |
| 2 | 0 | 7.4 | 50 | 2.7 | 100 | 2 |

The table 23 shows a methylation reaction (Product of a reaction) of an inorganic antimony.

TABLE 23

| | relative ratio | | | | | | conversion |
|---|---|---|---|---|---|---|---|
| No. | U1 (%) | U2 (%) | iSb (III) (%) | U3 (%) | U4 (%) | total (%) | ratio (%) |
| 1 | 7 | 0 | 0 | 23 | 70 | 100 | 110 |
| 2 | 63 | 37 | 0 | 0 | 0 | 100 | 45 |

Figure 33:
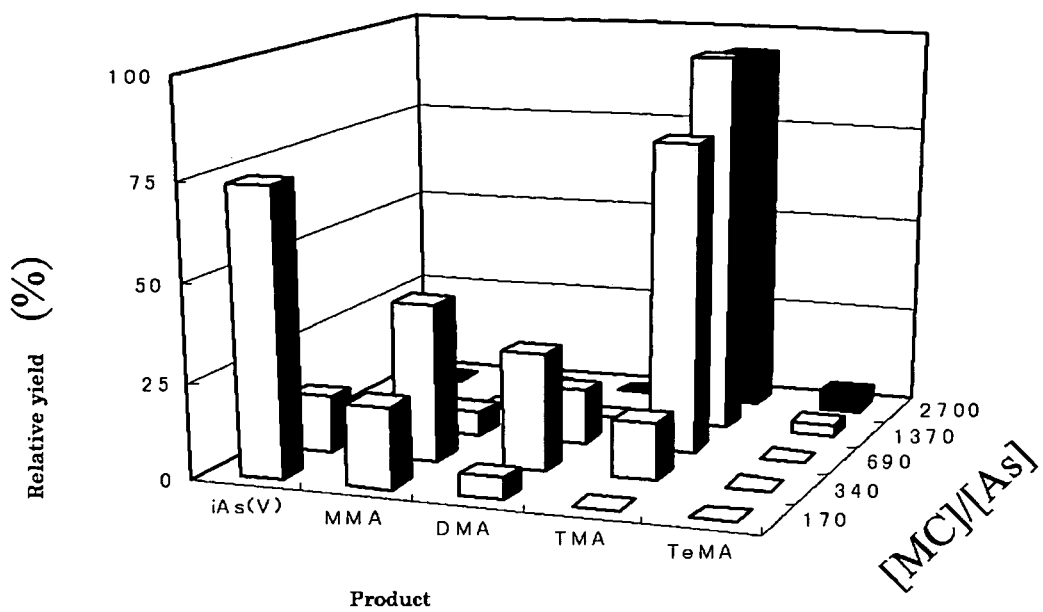
FIG. 33 gives a reaction condition in the production of trimechyl arsenic (TMA) from arsenic trioxide according to methylcobalamin.

(III)] by MC. In table, [GSH]: Molarity of the reducing agent (GSH), [MC]: Molarity of methylcobalamin, [As]: Molarity of arsenic trioxide which is a starting material, respectively. Furthermore, in the table, GSH: reduced glutathione, MC: methylcobalamin, As: starting material (It is trivalent arsenic here: iAs (III).), MMA: monomethylated arsenic acid, DMA: dimethylarsineoxide, TMAO: trimethylarsineoxide and TeMA: tetramethyl arsenic, respectively, a value was calculated as a conversion ratio=100% ([iAs (V)]+[MMA]+[DMA]+[TMAO]+[TeMA])/[iAs (III)]). Further, FIG. 33 gives a reaction condition in the production of trimechyl arsenic (TMA) from arsenic trioxide according to methylcobalamin.

TABLE 24

| | reactant | | | | mole fraction to arsenic | |
|---|---|---|---|---|---|---|
| No | GSH (µmol) | MC (µmol) | As (nmol) | Buffer (pH 8) (µL) | [GSH]/[As] | [MC]/[As] |
| 1 | 130.2 | 7.4 | 2.7 | 50 | 48222 | 2741 |
| 2 | 65.1 | 3.7 | 2.7 | 50 | 24111 | 1370 |
| 3 | 32.6 | 1.9 | 2.7 | 50 | 12056 | 685 |
| 4 | 16.3 | 0.9 | 2.7 | 50 | 6028 | 343 |
| 5 | 8.1 | 0.5 | 2.7 | 50 | 3014 | 171 |

TABLE 25

| | reaction condition | | product of a raction | | | | | | conversion ratio |
|---|---|---|---|---|---|---|---|---|---|
| | Temp. | Time | relative yield (%) | | | | | | |
| No. | (° C.) | (hr) | iAs (V) | MMA | DMA | TMAO | TeMA | total | (%) |
| 1 | 100 | 2 | 0 | 0 | 0 | 95 | 5 | 100 | 91 |
| 2 | 100 | 2 | 0 | 0 | 0 | 97 | 3 | 100 | 92 |
| 3 | 100 | 2 | 0 | 6 | 14 | 79 | 0 | 100 | 89 |
| 4 | 100 | 2 | 15 | 41 | 30 | 15 | 0 | 100 | 87 |
| 5 | 100 | 2 | 74 | 21 | 6 | 0 | 0 | 100 | 97 |

As it is clear from FIG. 32, it was revealed that the U1, U2, U3 and U4 attributing to the methylated antimony were generated by reacting the trivalent inorganic antimony with methylcobalamin. Therefore, it is recognized that it is also possible to obtain more harmless methylated antimony concerning antimony.

Example 21

Next, the effects were examined which a mole fraction of each component of the composition for alkylation gives. Specifically, experiment was carried out in the same manner as the above mentioned example with the use of GSH as the reducing agent, arsenic as the harmful compound and methylcobalamin as the cobalt complex. The result of this is shown in the tables 24 and 25. The table 24 shows a methylation reaction (Reacting substance) of arsenic trioxide [iAs (III)] by MC. The table 25 shows a methylation reaction (Reaction condition and product of a reaction) of arsenic trioxide [iAs As it is clear from the tables 24 and 25, in relative ratio, 90% or more of the harmless trimethylarsineoxide can be obtained in the case that 10000 folds or more of the reducing agent, GSH compared with arsenic is added and 1000 folds or more of methylcobalamin compared with arsenic is added. That is, it was revealed that in relative ratio, 90% or more of the harmless trimethylarsineoxide can be obtained in the case that it is [GSH]/[As]>1000, [MC]/[As]>100, more preferably, [GSH]/[As]>10000, [MC]/[As]>1000.

Industrial Applicability

The compositions of the present invention make it possible to produce a method of detoxifying the harmful compound more practically and industrially wherein the methods play a rule in the detoxification of the harmful compound containing arsenic etc. The present inventions make a significant contribution in the broad fields of treatments of the industrial waste etc., and environmental protections concerning a polluted mud or a soil, since the harmless compound obtained by converting the harmful compound containing arsenic etc., to more harmless compound by the alkylation are extremely stable and safe.

The invention claimed is:

1. A composition for alkylating a harmful compound containing at least one element selected from the group consisting of arsenic, antimony and selenium to detoxify the harmful compound, comprising:
a cobalt complex;
a first reducing agent that is capable of reducing at least one metal selected from the group consisting of arsenic, antimony and selenium,
a second reducing agent that is capable of reducing the cobalt complex and is at least one selected from the group consisting of titanium oxide and ruthenium complex,
at least one organic halide compound selected from the group consisting of methyl chloride, methyl bromide, methyl iodide, chloroacetic acid, bromoacetic acid, iodoacetic acid, chloroethanol, bromoethanol, iodoethanol, chloropropionic acid, bromopropionic acid, iodopropionic acid, chloroacetic acid ethyl ester, bromoacetic acid ethyl ester and iodoacetic acid ethyl ester,
wherein the composition is capable of alkylating a harmful compound containing at least one element selected from the group consisting of arsenic, antimony and selenium to detoxify the harmful compound, and
wherein the cobalt complex is at least one selected from
(1) an organometallic-cobalt complex having a cobalt-carbon bond comprising at least one compound selected from the group consisting of methylcobalamin (methylated vitamin B12, official name: Coα-[α-5,6-dimethyl-benz-1H-imidazole-1-yl-Coβ-methylcobamide]), vitamin B12, cobalt(II) acetyl acetonate, cobalt(III) acetyl acetonate, cobalt carbonyl (dicobalt octacarbonyl), cobalt(II) 1,1,1,5,5,5-hexafluoro acetyl acetonate, cobalt(II) meso-tetra phenyl porphin, hexafluoro phosphoric acid bis (pentamethyl cyclopenta dienyl) cobalt, N, N'-bis (salicylidene) ethylene diamine cobalt(II), bis (2,2,6,6-tetramethyl-3,5-heptanedionato) cobalt(II), (chlorophthalocyaninnato) cobalt(II), chlorotris (triphenylphosphine) cobalt(I), methyl complex of cobalt(II) acetate, cobalt(II) benzoate, cobalt(II) cyanide, cyclohexane cobalt(II) butyrate, 2-cobalt(II) ethylhexanoate, meso-tetramethoxyphenyl porphyrin cobalt(II), cobalt naphthenate, cobalt(II) phthalocyanine, methyl cobalt (III) protoporphyrin IX, cobalt stearate, cobalt(II) sulfamate, (1R, 2R)-(−)01,2-cyclohexanediamino-N,N'-bis (3,5-di-t-butylsalicylidene) cobalt(II), (1S, 2S)-(+)-1,2-cyclohexanediamino-N,N'-bis (3,5-di-t-butylsalicylidene) cobalt(II), cyclopentadienyl bis (triphenylphosphine) cobalt(I), cyclopentadienyl cobalt dicarbonyl, dibromo bis (triphenylphosphine) cobalt (II), (tetraaminochloro phthalocyaninnato) cobalt(II), and (tetra-t-butyl phthalocyaninnato) cobalt(II), and
(2) a cobalt-methyl complex formed by allowing a cobalt compound to coexist with an alkyl halide.

2. A composition according to claim 1, wherein the first reducing agent comprises a material having SH group as a reducing agent.

3. A composition according to claim 2, wherein the material having SH group is at least one selected from the group consisting of glutathione, reduced glutathione (GSH), cysteine, S-adenosyl cysteine, sulforaphane, homocysteine and thioglycol.

4. A composition according to claim 1, wherein the composition further comprises a methylating agent having S-Me group.

5. A composition according to claim 4, wherein the methylating agent is at least one selected from the group consisting of methionine and S-adenosyl methionine.

6. A composition according to claim 1, wherein the composition further comprises a buffer solution.

7. A composition according to claim 6, wherein a pH of the buffer solution is in the range of 5-10.

8. A composition according to claim 1, wherein the composition further comprises $H_2O_2$.

9. A composition according to claim 1, wherein the organic halide compound is at least one selected from the group consisting of methyl chloride, methyl bromide and methyl iodide.

10. A composition according to claim 1, wherein the organic halide compound is at least one selected from the group consisting of methyl iodide, methyl bromide, and methyl chloride.

11. A composition according to claim 1, wherein the organic halide compound is at least one selected from the group consisting of chloroacetic acid, bromoacetic acid, and iodoacetic acid.

12. A composition according to claim 1, wherein a molar ratio between the first reducing agent and at least one metal selected from the group consisting of arsenic, antimony and selenium expected to be present during use of the composition is greater than or equal to 1000.

13. A composition according to claim 12, wherein the ratio is greater than or equal to 10000.

14. A composition according to claim 1, wherein a molar ratio between the cobalt complex and at least one metal selected from the group consisting of arsenic, antimony and selenium expected to be present during use of the composition, is greater than or equal to 100.

15. A composition according to claim 14, wherein the ratio is greater than or equal to 1000.

16. A composition according claim 1, wherein vitamin B12 is cyanocobalamin.

* * * * *